US007550733B2

(12) United States Patent
Endo et al.

(10) Patent No.: US 7,550,733 B2
(45) Date of Patent: Jun. 23, 2009

(54) RADIATION IMAGING APPARATUS, APPARATUS CONTROL METHOD, AND COMPUTER-READABLE STORAGE MEDIUM STORING PROGRAM FOR EXECUTING CONTROL

(75) Inventors: Tadao Endo, Honjo (JP); Toshio Kameshima, Kumagaya (JP); Tomoyuki Yagi, Honjo (JP); Katsuro Takenaka, Kodama-gun (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 291 days.

(21) Appl. No.: 11/692,534

(22) Filed: Mar. 28, 2007

(65) Prior Publication Data

US 2008/0011958 A1 Jan. 17, 2008

(30) Foreign Application Priority Data

Apr. 21, 2006 (JP) ............................. 2006-118324

(51) Int. Cl.
*G01T 1/24* (2006.01)

(52) U.S. Cl. ....................... 250/370.09; 378/4; 378/98.8

(58) Field of Classification Search ............ 250/370.09, 250/370.11; 378/4, 98.8
See application file for complete search history.

(56) References Cited

U.S. PATENT DOCUMENTS

| 6,952,015 | B2 | 10/2005 | Kameshima | ............ 250/370.11 |
| 6,952,464 | B2 | 10/2005 | Endo | ........................ 378/98.11 |
| 6,985,555 | B2 | 1/2006 | Endo | ........................ 378/98.11 |
| 7,002,157 | B2 | 2/2006 | Kameshima | ............ 250/370.11 |
| 7,012,260 | B2 | 3/2006 | Endo | ...................... 250/370.11 |
| 7,078,703 | B2* | 7/2006 | Watanabe | ............... 250/370.15 |
| 7,138,639 | B2 | 11/2006 | Kameshima | ............ 250/370.11 |
| 7,154,099 | B2 | 12/2006 | Endo | ...................... 250/370.11 |
| 7,227,926 | B2 | 6/2007 | Kameshima et al. | ....... 378/98.9 |
| 2002/0017610 | A1* | 2/2002 | Takemoto | .............. 250/370.09 |
| 2005/0109927 | A1 | 5/2005 | Takenaka et al. | ......... 250/252.1 |
| 2005/0199834 | A1 | 9/2005 | Takenaka et al. | ............ 250/580 |
| 2005/0200720 | A1 | 9/2005 | Kameshima et al. | ..... 348/220.1 |

(Continued)

FOREIGN PATENT DOCUMENTS

JP          11-9579          1/1999

(Continued)

*Primary Examiner*—David P. Porta
*Assistant Examiner*—Mark R Gaworecki
(74) *Attorney, Agent, or Firm*—Fitzpatrick, Cella, Harper & Scinto

(57) ABSTRACT

To provide a radiation imaging apparatus which is capable of both connecting state radiographing for radiographing with a C arm connected and non-connecting state radiographing for radiographing with the C arm disconnected, and is convenient and obtains high quality images, the apparatus includes: a flat panel detector; a holding unit for holding at least the flat panel detector; and a control unit for controlling the flat panel detector. With this configuration, the flat panel detector can be connected to and disconnected from the holding unit; connecting state radiographing can be performed with the flat panel detector connected to the holding unit, and non-connecting state radiographing can be performed with the flat panel detector disconnected from the holding unit; the control unit controls the flat panel detector such that a heat generation quantity of the flat panel detector during the non-connecting state radiographing can be lower than a heat generation quantity of the flat panel detector during the connecting state radiographing.

14 Claims, 22 Drawing Sheets

CONNECTING STATE

U.S. PATENT DOCUMENTS

| | | | |
|---|---|---|---|
| 2005/0220269 A1 | 10/2005 | Endo et al. | 378/114 |
| 2006/0119719 A1 | 6/2006 | Kameshima | 348/308 |
| 2006/0192130 A1 | 8/2006 | Yagi | 250/370.14 |
| 2006/0289774 A1 | 12/2006 | Endo et al. | 250/370.09 |
| 2007/0040099 A1 | 2/2007 | Yokoyama et al. | 250/208.1 |
| 2007/0069144 A1 | 3/2007 | Kameshima | 250/370.09 |
| 2007/0080299 A1 | 4/2007 | Endo et al. | 250/370.09 |
| 2007/0096032 A1 | 5/2007 | Yagi et al. | 250/370.11 |
| 2007/0125952 A1 | 6/2007 | Endo et al. | 250/369 |
| 2007/0131843 A1 | 6/2007 | Yokoyama et al. | 250/205 |
| 2007/0183573 A1 | 8/2007 | Kameshima et al. | 378/98.9 |
| 2007/0210258 A1 | 9/2007 | Endo et al. | 250/370.09 |

FOREIGN PATENT DOCUMENTS

| | | |
|---|---|---|
| JP | 2005-470 | 1/2005 |

\* cited by examiner

CONNECTING STATE

DISCONNECTING STATE

RADIATION IMAGING APPARATUS, APPARATUS CONTROL METHOD, AND COMPUTER-READABLE STORAGE MEDIUM STORING PROGRAM FOR EXECUTING CONTROL

BACKGROUND OF THE INVENTION

1. Field of the Invention

The present invention relates to a radiation detection system for use in diagnoses in a hospital, and a radiation imaging apparatus appropriate as an industrial non-destructive inspection apparatus. In this specification, electromagnetic waves such as X-rays, γ-rays, etc., as well as particulate beams such as α-rays, and β-rays are included in "radiation".

2. Description of the Related Art

With the progress of recent thin film semiconductor processing technology for radiography, apparatuses have been developed for radiographing an X-ray image using a semiconductor sensor. These X-ray detectors can be produced in a relatively flat structure, and is referred to as a flat panel X-ray detector (flat panel detector) (FPD). The FPD can be an indirect FPD and a direct FPD. The indirect FPD converts X-rays into visible light through a phosphor, and detects the light using an amorphous optoelectronic conversion element and a switch element. The direct FPD does not use a phosphor, but uses amorphous selenium and the like, converts X-rays directly into electrons, and detects them using an amorphous silicon switch element (TFT).

Presently, an image intensifier (I. I.) has become widespread as a common detector for fluoroscopic radiography. The I. I. converts X-rays into visible light by a scintillator, then converts the optoelectronically intensified secondary electrons into visible light again, thereby obtaining an image by a CCD camera. Generally, since the I. I. has high sensitivity, it has been used for a patient to reduce the dosage of exposure to radiation when relatively long time fluoroscopic radiography is required in performing, for example, fluoroscopic radiographing for gastric surgery, surgery on the heart or brain, etc., while inserting a catheter into veins, and the like.

On the other hand, since a system using the FPDs can momentarily convert an X-ray image into digital data, it has become widespread as a radiographing apparatus capable of performing fluoroscopic radiographing. Although the I. I. has the advantage of high X-ray sensitivity, it also has some problems of, for example, halation at high dosage of exposure to radiation because of a narrow dynamic range, distorted surrounding images by an electronic lens, poor durability, a heavy device, etc.

To overcome the above-mentioned problems, a new fluoroscopic radiographing detector as a new replacement for the I. I. can be an FPD having a wide dynamic range, less image distortion, and less degradation. A mobile X-ray imaging apparatus using such an FPD is disclosed in Japanese Patent Application Laid-Open No. 2005-000470.

Additionally, Japanese Patent Application Laid-Open No. 11-009579 discloses an X-ray imaging apparatus that has a mechanism of connecting to and disconnecting from an X-ray detection unit for a C arm, and can easily exchange various flat panel detectors having different capabilities and specifications in radiograph size, resolution, etc.

SUMMARY OF THE INVENTION

Generally, when fluoroscopic radiographing is performed, a pulse generating radiation source is used to reduce the dosage of exposure to radiation for a patient. The source can be of a rotating anode type capable of suppressing heat generation by rotating an anode member called a target for triggering off collision between accelerated electrons for generation of X-rays, and of a fixed anode type without rotation. The X-ray generation apparatus (radiation source) of the rotating anode type can generate X-rays of high dosage, and is appropriate for high-speed fluoroscopic radiographing. By contrast, since the X-ray generation apparatus of the fixed anode type cannot generate large amount of X-rays instantaneously, it is not appropriate for high-speed radiographing.

In any case, there is the problem of heat generation from a radiation source because it is necessary to irradiate an object with plural times of emission of X-ray pulses for several seconds to several minutes, or for a longer time, in fluoroscopic radiographing.

Additionally, the FPD generally reads an electrical signal obtained by converting an X-ray into signal charge through an amorphous silicon switch element (TFT). Therefore, it requires a driving circuit unit for driving a TFT and a read out circuit unit for detecting a signal through the TFT. In a medical device for reading low X-ray signal charge, strict specifications and reliability far advanced from consumer products are required. The read out circuit unit is provided with an operational amplifier for each signal wiring, and one read out circuit is configured by a number of operational amplifiers. Generally, a radiographic area requested for a flat panel X-ray detector depends on a radiographed portion, that is, as a square, it is a 20 to 25 cm square for a heart, a 30 to 35 cm square for a stomach portion, and a 35 to 45 cm square for a chest portion. If a 41 cm square X-ray detection element is configured with 160 μm pitches, 2560×2560 picture elements are required. When a read out circuit unit is prepared for such a large number of picture elements generated in thin film semiconductor processing, an integrated circuit (IC, LSI) in common semiconductor technology is generated. However, plural divided read out circuit units are used due to the size of a silicon wafer and the semiconductor process for generating it. For example, 40 chips are required for 64 channels, 20 chips are required for 128 channels, and 10 chips are required for 256 channels. The driving circuit unit is designed in the same manner.

To attain a high S/N ratio, each input unit (initial stage portion) of the read out circuit unit is to be configured by an operational amplifier. Especially when fluoroscopic radiographing is performed, it is necessary to provide an operational amplifier for the initial and subsequent stage portions to reduce the dosage of exposure to radiation so that the X-ray detection signal can be amplified. For example, in the case of a 256-channel IC, 10 chips are to be provided with 512 or more operational amplifiers for each chip. Then, the power consumption soars, and the problem of heat generation from the flat panel X-ray detector arises.

When the heat generated from the IC is applied to the flat panel X-ray detector, the dark current of the X-ray detection element increases, and the leak current of the TFT element also increases, thereby causing the increase in noise. These conditions degrades the graininess of an image, causes an artifact which is not the information about an object, thereby exceedingly degrading the image quality. That is, it is the problem of reducing the efficiency of an X-ray image diagnosis.

Furthermore, in the fluoroscopic radiographing, the X-ray detector has to be driven for several seconds to several minutes, or longer depending on each case. Therefore, as compared with still image drive, the heat generation from the X-ray detector, especially from the read out circuit unit and the AD conversion circuit unit (ADC) cannot be ignored. Furthermore, in the fluoroscopic radiographing, it is necessary to increase the number of ADCs as compared with still images, thereby possibly increasing the heat generation from the ADC.

Furthermore, in the fluoroscopic radiographing, when it is necessary to transmit the digital data converted by the ADC to the body several meters to tens meter apart, a line driver and a line receiver are required in transmitting the digital data at a high speed, which also causes the problem of heat generation from the electric parts.

Furthermore, in the state of the FPD connected to the C arm, heat is conducted and radiated by exchange through the connection point with the C arm while the heat radiation environment becomes poor in the state of the FPD separated from the C arm. Therefore, the heat generation of FPD is a problem in the state of the FPD separated from the C arm.

The present invention has been developed to solve the above-mentioned problems and the objective of the present invention is to provide a radiation imaging apparatus capable of reducing undesired influence by the heat generation of the FPD in the state of the FPD separated from the C arm, and capable of performing radiographing both in the state of the FPD connected to the C arm and in the state of the FPD separated from the C arm.

The present invention aims at providing a radiation imaging apparatus capable of easily obtaining high quality images and both connecting state radiographing performed in the C arm connected state and non-connecting state radiographing performed in the C arm disconnected state.

The radiation imaging apparatus according to the present invention includes a flat panel detector, a holding unit for holding at least the flat panel detector, and a control unit for controlling the flat panel detector. With the configuration, the flat panel detector can be connected to and disconnected from the holding unit, connecting state radiographing can be performed with the flat panel detector connected to the holding unit, and non-connecting state radiographing can be performed with the flat panel detector disconnected from the holding unit, the control unit controls the flat panel detector such that a heat generation quantity of the flat panel detector during the non-connecting state radiographing can be lower than a heat generation quantity of the flat panel detector during the connecting state radiographing.

A method of controlling a radiation imaging apparatus according to the present invention includes having a flat panel detector, a holding unit for holding at least the flat panel detector, capably connecting the flat panel detector to and disconnected it from the holding unit, performing connecting state radiographing with the flat panel detector connected to the holding unit, and performing non-connecting state radiographing with the flat panel detector disconnected from the holding unit. With the configuration, the flat panel detector is controlled such that a heat generation quantity of the flat panel detector during the non-connecting state radiographing can be lower than a heat generation quantity of the flat panel detector during the connecting state radiographing.

The method of controlling the radiation imaging apparatus according to the present invention controls the flat panel detector such that power consumption of the flat panel detector during the non-connecting state radiographing can be lower than power consumption of the flat panel detector during the connecting state radiographing.

A computer-readable storage medium storing a program used to direct a computer to control the radiation imaging apparatus according to the present invention allows the computer to control the radiation imaging apparatus to have a flat panel detector, a holding unit for holding at least the flat panel detector, capably connect the flat panel detector to and disconnected it from the holding unit, perform connecting state radiographing with the flat panel detector connected to the holding unit, and perform non-connecting state radiographing with the flat panel detector disconnected from the holding unit. With the configuration, the program allows the computer to control the flat panel detector such that a heat generation quantity of the flat panel detector during the non-connecting state radiographing can be lower than a heat generation quantity of the flat panel detector during the connecting state radiographing.

The computer-readable storage medium storing a program used to direct a computer to control the radiation imaging apparatus according to the present invention allows the computer to control the flat panel detector such that power consumption of the flat panel detector during the non-connecting state radiographing can be lower than power consumption of the flat panel detector during the connecting state radiographing.

According to the present invention, the heat generation quantity of the flat panel detector can be suppressed even if the heat radiation environment of the flat panel detector is poor during the non-connecting state radiographing.

Further features of the present invention will become apparent from the following description of exemplary embodiments with reference to the attached drawings.

DESCRIPTION OF THE EMBODIMENTS

The mode for embodying the present invention is practically described below by referring to the attached drawings.

(First Mode for Embodying the Present Invention)

Figure 1:
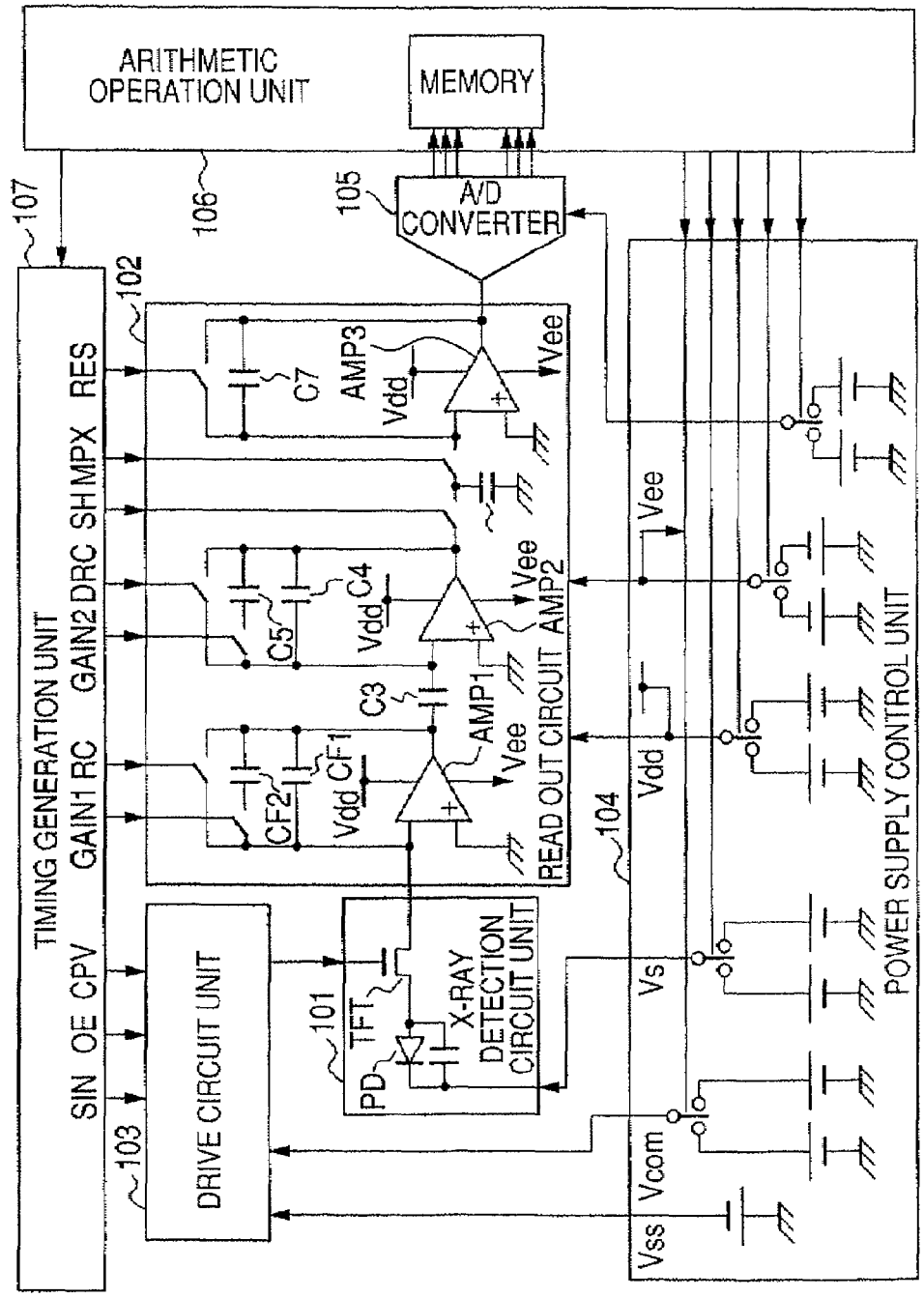
FIG. 1 illustrates the configuration of the circuit of the X-ray detector in the X-ray imaging apparatus according to the first mode for embodying the present invention.

FIG. 1 illustrates the configuration of the circuit of the flat panel X-ray detector (radiation imaging apparatus) according to the first mode for embodying the present invention. A picture element 101 is configured mainly by an optoelectronic conversion element (PD), and a switch element (TFT). The PD can be an X-ray detection element for converting an X-ray directly into electric charge or a photodiode for converting visible light into charge. When it is a photodiode, a phosphor (not illustrated in the attached drawings) for temporarily converting an X-ray into visible light is required. The optoelectronic conversion element PD is biased by the voltage Vs from a power supply control unit 104, and the gate voltage of the TFT is driven by the signal from a drive circuit unit 103. The drive circuit unit 103 is a shift register. The gate-on voltage (gate voltage) of the TFT is determined by the voltage Vcom applied from the power supply control unit 104 to the drive circuit unit 103. The gate-off voltage of the TFT is determined by the voltage Vss applied also from the power supply control unit 104 to the drive circuit unit 103. The signal of the optoelectronic conversion element PD is output to a read out circuit unit 102 through the TFT.

The initial stage portion of the read out circuit unit 102 is configured by an operational amplifier (AMP1), and is an integration circuit. Capacitors CF1 and CF2 in the integration circuit of the operational amplifier AMP1 can be switched by a signal GAIN1 from a timing generation unit 107. The output of the operational amplifier AMP1 is input to the operational amplifier (AMP2) at the next stage through the capacitor C3. Capacitors C4 and C5 connected to the feedback terminal of the operational amplifier AMP2 can be switched by a signal GAIN2, and the amplification rate (gain) of the operational amplifier AMP2 can be selected. The output of the operational amplifier AMP2 is accumulated by a capacitor C6 for sampling and holding, and is then output to an AD conversion unit 105 through an operational amplifier (AMP3) at the subsequent stage. The AD converted digital data is stored in the memory of an arithmetic operation unit 106. The operational amplifiers AMP1, AMP2 and AMP3 are operated by a "+" side power supply voltage Vdd and a "−" power supply voltage Vee. The power supply voltage of the AD conversion unit 105 is Vcc. The timing generation unit 107 provides a digital signal required by the drive circuit unit 103 and the read out circuit unit 102. The arithmetic operation unit 106 includes a CPU, and contains memory.

In the present mode for embodying the present invention, at an instruction from the arithmetic operation unit 106 containing the CPU, each power supply in the power supply control unit 104 can provide plural power supply voltages. The X-ray imaging apparatus illustrated in FIG. 1 has the configuration of connecting it to the end portion of a C-shaped support arm (C arm) 16 as illustrated in FIG. 19, and is also configured to perform radiographing with the arm disconnected from the apparatus as illustrated in FIG. 20.

Figure 19:
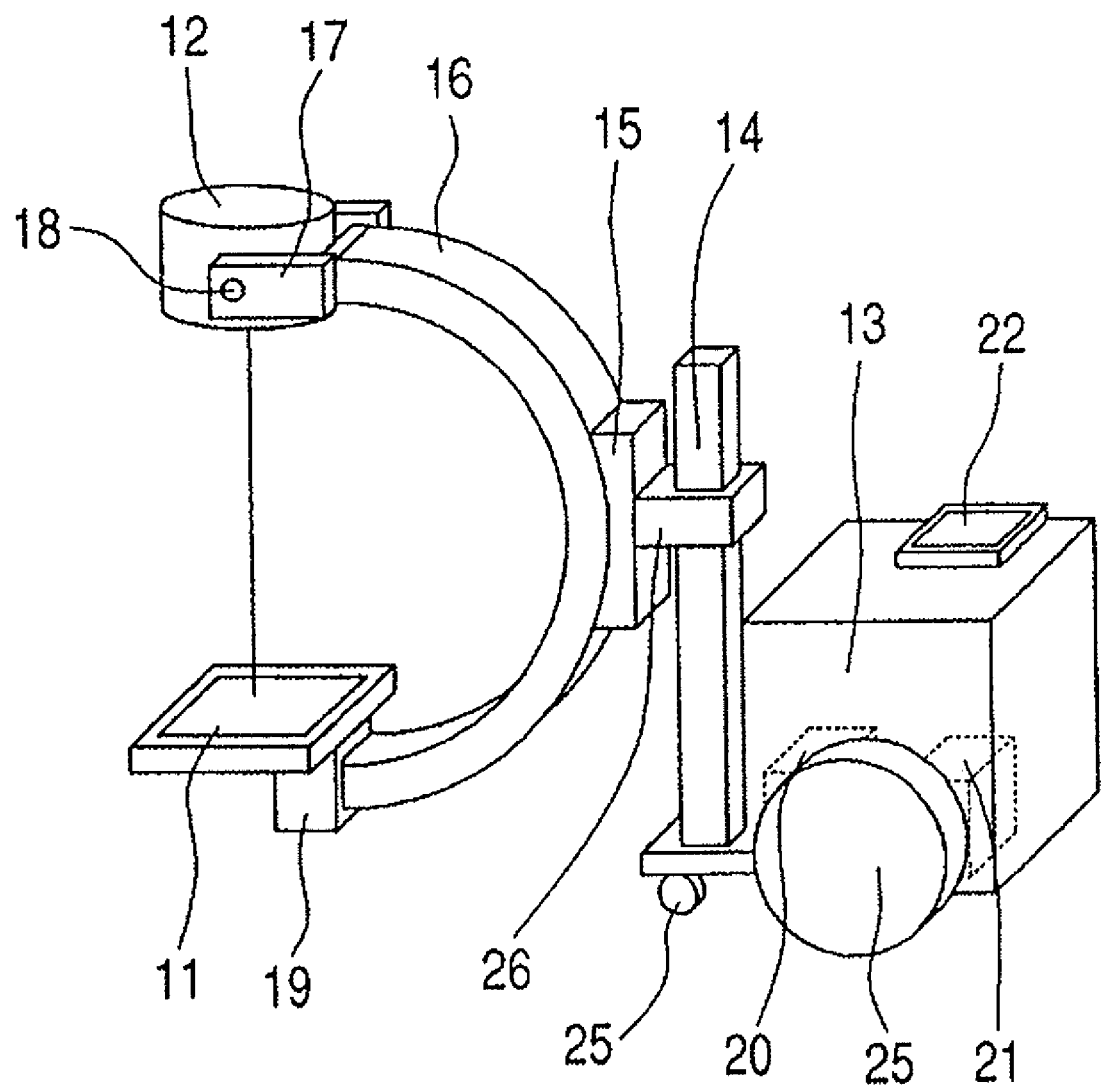
FIG. 19 illustrates the outline of the mobile X-ray imaging apparatus to which the present invention can be applied.
Figure 20:
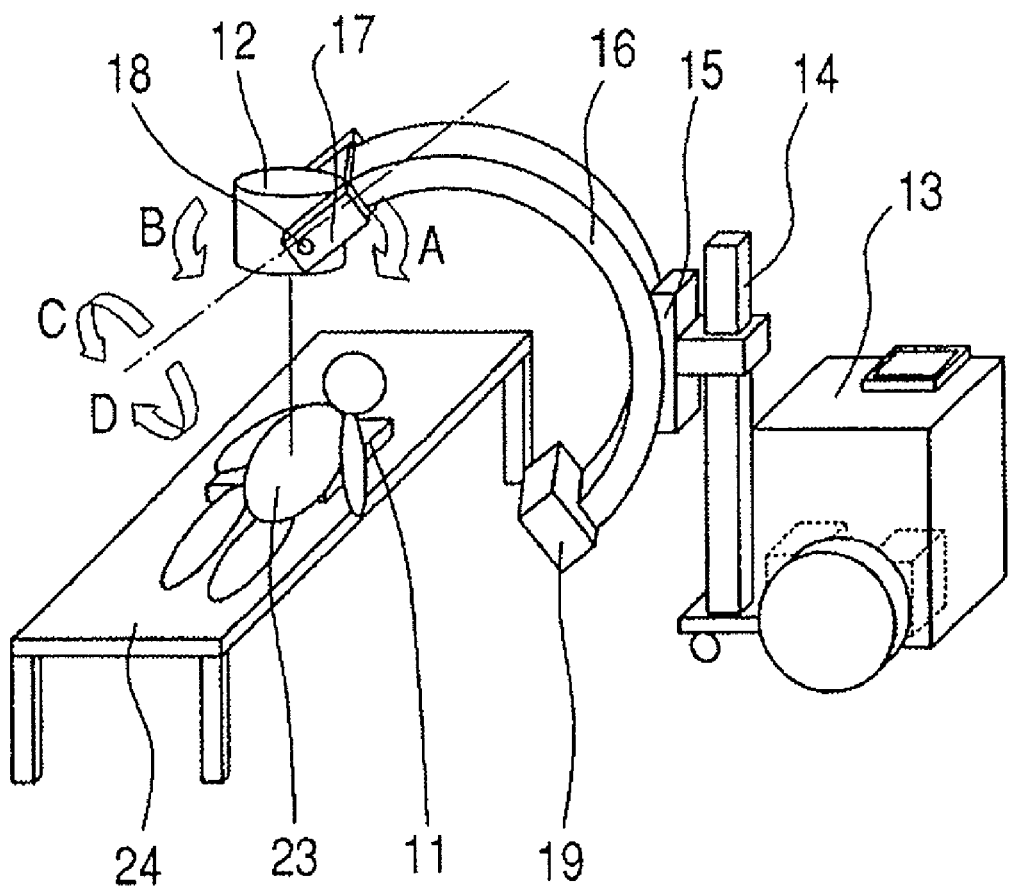
FIG. 20 illustrates the outline of the mobile X-ray imaging apparatus to which the present invention can be applied.

FIGS. 19 and 20 illustrate the mobile X-ray imaging apparatus applicable to the X-ray imaging apparatus according to the present invention. A flat panel X-ray detector 11 includes an X-ray detection sensor having a detection plane on which a plurality of optoelectronic conversion elements is arranged in a two-dimensional array, and an electrical component unit. The flat panel X-ray detector 11 is connected to a connection mechanism 19. A radiation source 12 is fixed through a pair of support panels 17.

As illustrated in the figures, the radiation source 12 and the flat panel X-ray detector are fixed to the C-shaped support arm (C arm) 16. The C arm 16 is connected to a column 14 through connection mechanisms 15 and 26. With the configuration, the radiation source 12 is fixed with the center of the emitted X-rays matching the center of the detection plane of the image detection unit 11.

The C arm 16 can be turned clockwise or counterclockwise using the connection mechanisms 14 and 15, and moved upwards and downwards along the column 14, thereby improving the convenience during radiographing. A mobile X-ray generation apparatus 13 has wheels 25, and can be moved in a hospital. A control unit 20 controls the X-ray generation apparatus, a control unit 21 controls the flat panel X-ray detector, and reference numeral 22 designates an operation and display unit.

FIG. 20 illustrates the state in which the flat panel X-ray detector 11 is removed from the connection mechanism 19 as a change from the state illustrated in FIG. 19. The flat panel X-ray detector 11 is mounted between a bed 24 and an object 23 laying on the bed 24 on his or her back. When the flat panel X-ray detector 11 is removed from the connection mechanism 19, wireless communication can be performed to and from the control unit 21, and a control signal and image data are communicated by wireless. The radiation source 12 is aligned above the flat panel X-ray detector 11 at the position where the X-rays can be emitted perpendicularly to the detection plane of the flat panel X-ray detector 11.

For the alignment, the C arm 16 rotates counterclockwise roughly 45° within the face of paper from the position illustrated in FIG. 20. The radiation source 12 rotates clockwise roughly 45° (A direction) from the position illustrated in FIG. 19 on the support panel 17 using a support axis 18 as the rotation center. The rotation can be made counterclockwise (B direction) depending on the conditions. The radiation source 12 can also be rotated in the C and D directions on the tangent of the arc of the C arm 16 as well as the support panel 17. The column 14 can also be rotated on the vertical axis, and the entire C arm 16 can be rotated on the vertical axis. Since the radiation source 12 can be moved with the degree of freedom, the image detection unit can be disconnected from the fixed mechanism so that X-rays can be irradiated at an appropriate position anywhere the unit is mounted.

In FIG. 19, the C arm (holding unit) 16 holds the flat panel X-ray detector 11 and the radiation source 12. The flat panel X-ray detector 11 can be connected to and disconnected from the C arm 16. Both the connecting state radiographing with the flat panel X-ray detector 11 connected to the C arm 16 and the non-connecting state radiographing with the flat panel X-ray detector 11 disconnected from the C arm 16 can be performed. The arithmetic operation unit 106 and the power supply control unit 104 control the flat panel X-ray detector 11 such that the heat generation quantity of the flat panel X-ray detector 11 during the non-connecting state radiographing can be lower than the heat generation quantity of the flat panel X-ray detector 11 during the connecting state radiographing. Practically, the arithmetic operation unit 106 and the power supply control unit 104 control the flat panel X-ray detector 11 such that the power consumption of the flat panel X-ray detector 11 during the non-connecting state radiographing can be lower than the power consumption of the flat panel X-ray detector 11 during the connecting state radiographing. Preferably, they perform control such that the power consumption of the read out circuit unit 102 during the non-connecting state radiographing can be lower than the power consumption of the read out circuit unit 102 during the connecting state radiographing.

The radiographing performed when the flat panel X-ray detector is connected to the C arm 16 as illustrated in FIG. 19 is referred to as "connecting state radiographing", and the X-ray radiographing performed when the flat panel X-ray detector is disconnected from the C arm 16 as illustrated in FIG. 20 is referred to as "non-connecting state radiographing". In the connecting state radiographing and the non-connecting state radiographing, at least one of the sensor bias Vs in the power supply control unit 104, the TFT on voltage Vcom, the power supply voltages Vdd and Vss of the operational amplifier in the read out circuit unit 102, and the power supply voltage of the AD conversion unit 105 is switched. That is, in the non-connecting state radiographing, as compared with the connecting state radiographing, control is performed such that the power supplied to the flat panel X-ray detector can be lower (the power supply voltage van be lower), and the heat generation quantity during the non-connecting state radiographing is suppressed as compared with the connecting state radiographing.

The arithmetic operation unit 106 and the power supply control unit 104 control the flat panel X-ray detector 11 such that the power supply voltages Vdd and Vee of the read out circuit unit 102 during the non-connecting state radiographing can be lower than the power supply voltages Vdd and Vss of the read out circuit unit 102 during the connecting state radiographing. Furthermore, they control the flat panel X-ray detector 11 such that the bias Vs of the conversion element PD or the drive voltage Vcom of he switch element TFT during the non-connecting state radiographing can be lower than bias Vs of the conversion element PD or the drive voltage Vcom of the switch element TFT during the connecting state radiographing.

The X-ray imaging apparatus conducts heat and radiate the heat by exchange through connection points to the C arm with the flat panel X-ray detector 11 connected to the C arm. The details are described below by referring to FIG. 18. When the flat panel X-ray detector 11 is not connected to the C arm, the heat radiation environment is poor. Therefore, in the present mode for embodying the present invention, when the flat panel X-ray detector 11 is not connected to the C arm, the voltage of the flat panel X-ray detector 11 is reduced, the power supply is reduced, and the heat generation quantity is suppressed as compared with the state in which the flat panel X-ray detector 11 is connected.

Generally, the voltages Vdd and Vss depend on the production process of an operational amplifier. If a power supply voltage is changed, various characteristics of the amplifier also change in many cases. For example, the operational amplifier AMP1 accumulates a signal from the picture element 101 in the capacitor CF1, but the amount of charge accumulated in the capacitor CF1 changes if the power supply voltage of the operational amplifier AMP1 drops. That is, what is called a dynamic range changes. In this case, during the connecting state radiographing and the non-connecting state radiographing, not only the power supply voltage, but also the capacitor CF2 can be added for use. That is, when the characteristic by a change of a power supply voltage changes, it is to be grasped in advance, and the drive to compensate for it is to be performed.

There can be a case in which a power supply voltage cannot be largely changed with respect to the reliability of an operational amplifier. In this case, the precision of the power supply of the power supply control unit 104 is to be improved, and can be switched in the range of the recommended operation condition (for example, 5 V±0.5).

The power supply Vcc of the AD conversion unit 105 is similar to Vdd and Vss. The Vs of the picture element 101 does not require an enormously large amount of current as compared with the operational amplifier. However, since there are a large number of picture elements, and the X-ray detection element and the switch element have temperature characteristics, it is desired that the power supply control unit 104 changes the power consumption between the connecting state radiographing and the non-connecting state radiographing.

Especially, when a direct X-ray detection element is used, 0.5 to 1 mm thick amorphous selenium is generally evaporated. Therefore, a higher electric field is required than the indirect type, and the voltage of 5000 to 10000 volts is to be applied to the bias Vs applied to the X-ray detection element. In the present mode for embodying the present invention, the Vs power supply voltage in the non-connecting state radiographing can be switched to avoid the problem of heat generation by the high voltage.

Furthermore, by reducing the power supply voltage of the read out circuit unit 102, the dynamic range of the read out circuit unit 102 is reduced. To compensate for the reduction, Vs and Vcom can be reduced.

Figure 2:
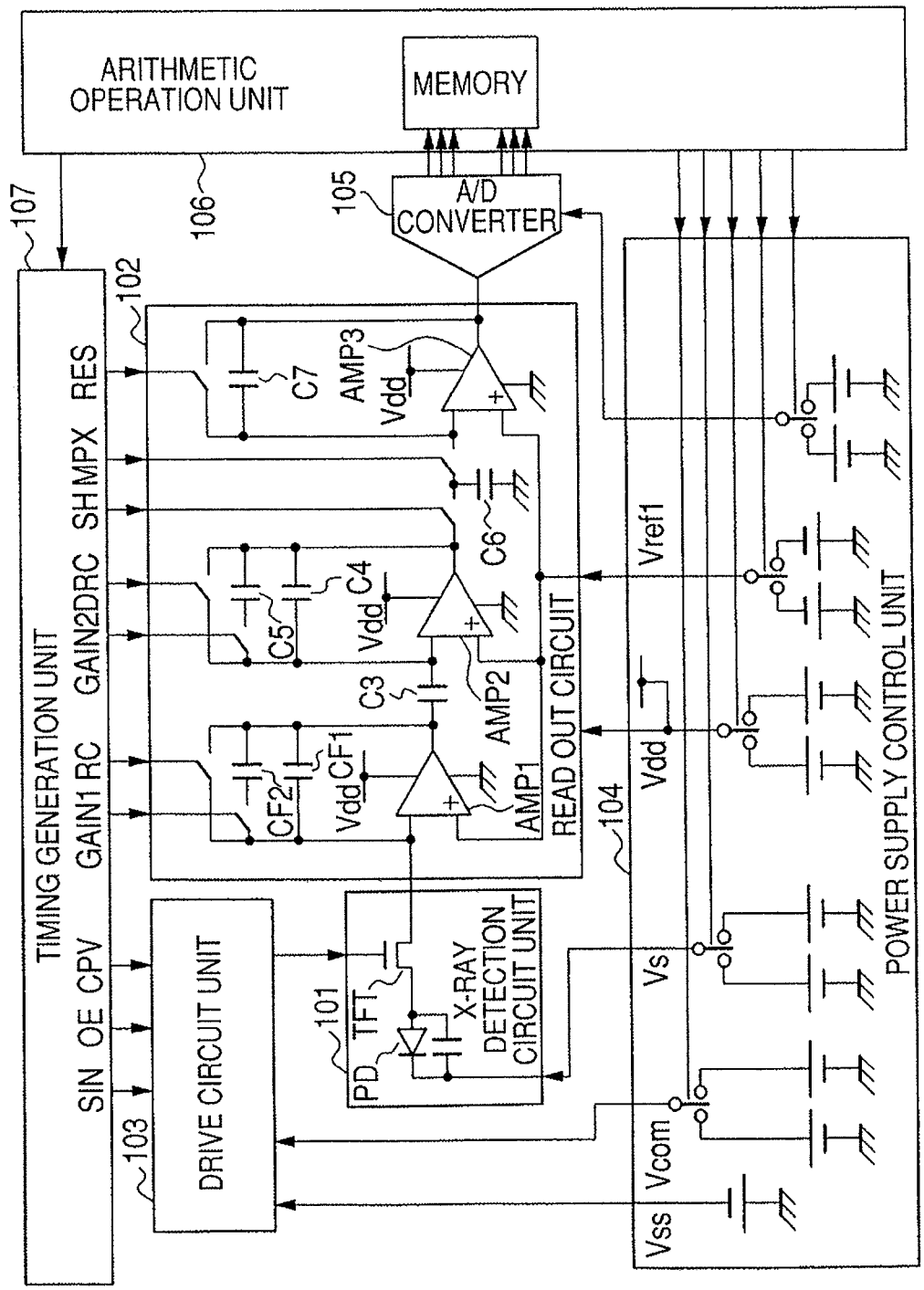
FIG. 2 illustrates the configuration of the circuit of the X-ray detector in the X-ray imaging apparatus according to the first mode for embodying the present invention.

FIG. 2 illustrates the configuration of the circuit of the flat panel X-ray detector in the X-ray imaging apparatus according to the first mode for embodying the present invention, and illustrates a circuit other than the circuit illustrated in FIG. 1. In FIG. 2, a circuit member also illustrated in FIG. 1 is assigned the same reference numeral.

The different point of FIG. 2 as compared with FIG. 1 is that the operational amplifier (AMP1, AMP2, and AMP3) in the read out circuit unit 102 is operated by a single power supply (Vdd), and the reference potential (Vref1) connected to the non-inversion input terminal of each operational amplifier is supplied from the power supply control unit 104. As described above by referring to FIG. 1, during the non-connecting state radiographing, the power supply voltage Vdd is reduced and driven with the supply of power reduced, and the heat generation is suppressed. Then, if the corresponding reduction of the dynamic range and other inconvenient factors occur, the reference potential Vref1 of the power supply control unit 104 can be changed. Furthermore, in FIG. 2, the Vref1 common line supplies the reference potential of the operational amplifiers AMP1, AMP2, and AMP3. However, as necessary, another system can supply the potential. In this case, the power supply control unit 104 provides three types of reference potential (Vref1, Vref2, and Vref3) are provided, and each of them can be independently switched.

Figure 3:
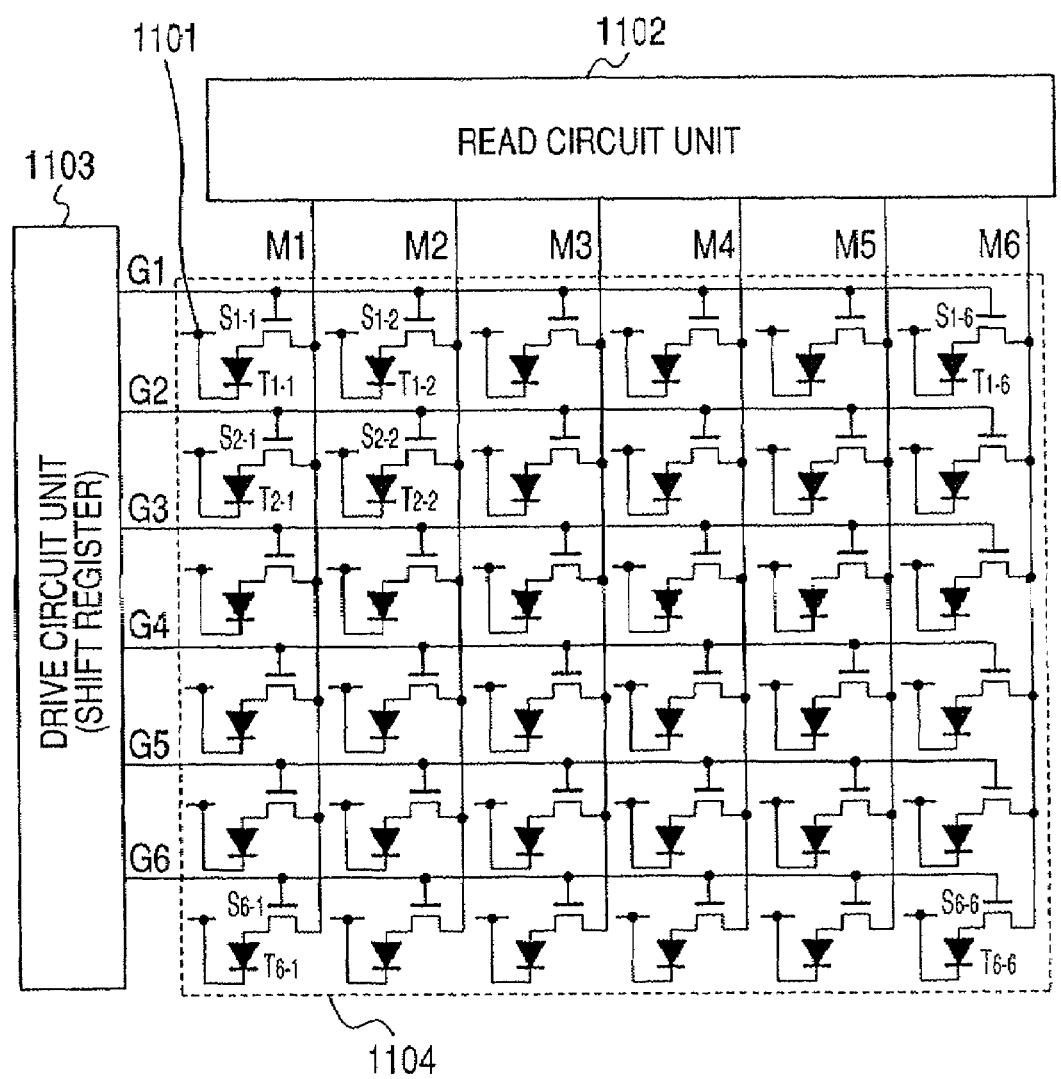
FIG. 3 illustrates the two-dimensional expression of the picture elements illustrated in FIGS. 1 and 2.

FIG. 3 illustrates the picture element 101 illustrated in FIG. 1 as the two-dimensional expression of 6×6=36 picture elements. For example, to medically radiograph the chest portion of a person, for example, the resolution of about 160 μm pitches is required for a photoreceiving area of, for example, 41 cm×41 cm. In the case of 160 μm pitches for a photoreceiving area of 41 cm×41 cm, the number of picture elements is 2560×2560, that is, about 6.55 million picture elements.

In FIG. 3, S1-1 to S6-6 designate an optoelectronic conversion element or an X-ray detection element (radiation detection element). In the indirect system, the material is amorphous silicon. In the direct system, the material is amorphous selenium. The radiation detection element is biased by a sensor bias source Vs 1101. T1-1 to T6-6 designate switch elements, and are generally made of amorphous silicon thin film transistor TFT regardless of the direct or indirect system. G1 to G6 designate driving gate wiring for driving the TFT, and M1 to M6 designate read wiring for reading a signal of a radiation detection element through the TFT. G1 to G6 are driven by a drive circuit unit 1103 configured mainly by a shift register circuit. The read wiring M1 to M6 are read by the read circuit unit 1102. The X-ray detection elements S1-1 to S6-6, the switch elements T1-1 to T6-6, the gate wiring G1 to G6, and the signal wiring M1 to M6 are collectively referred to as a radiation detection circuit unit (radiation detection substrate) 1104.

The picture elements include conversion elements S1-1 to S6-6 that are arranged in a matrix array of rows and columns on the radiation detection substrate 1104 and convert radiation into an electrical signal, and switch elements T1-1 to T6-6. The drive wiring G1 to G6 are connected to the switch elements T1 to T6-6 in the row direction. The signal wiring M1 to M6 are connected to the switch elements S1-1 to S6-6 in the column direction, and transmit the electrical signal. The drive circuit unit 1103 is connected to the drive wiring G1 to G6. The read circuit unit 1102 is connected to the signal wiring M1 to M6.

Figure 4:
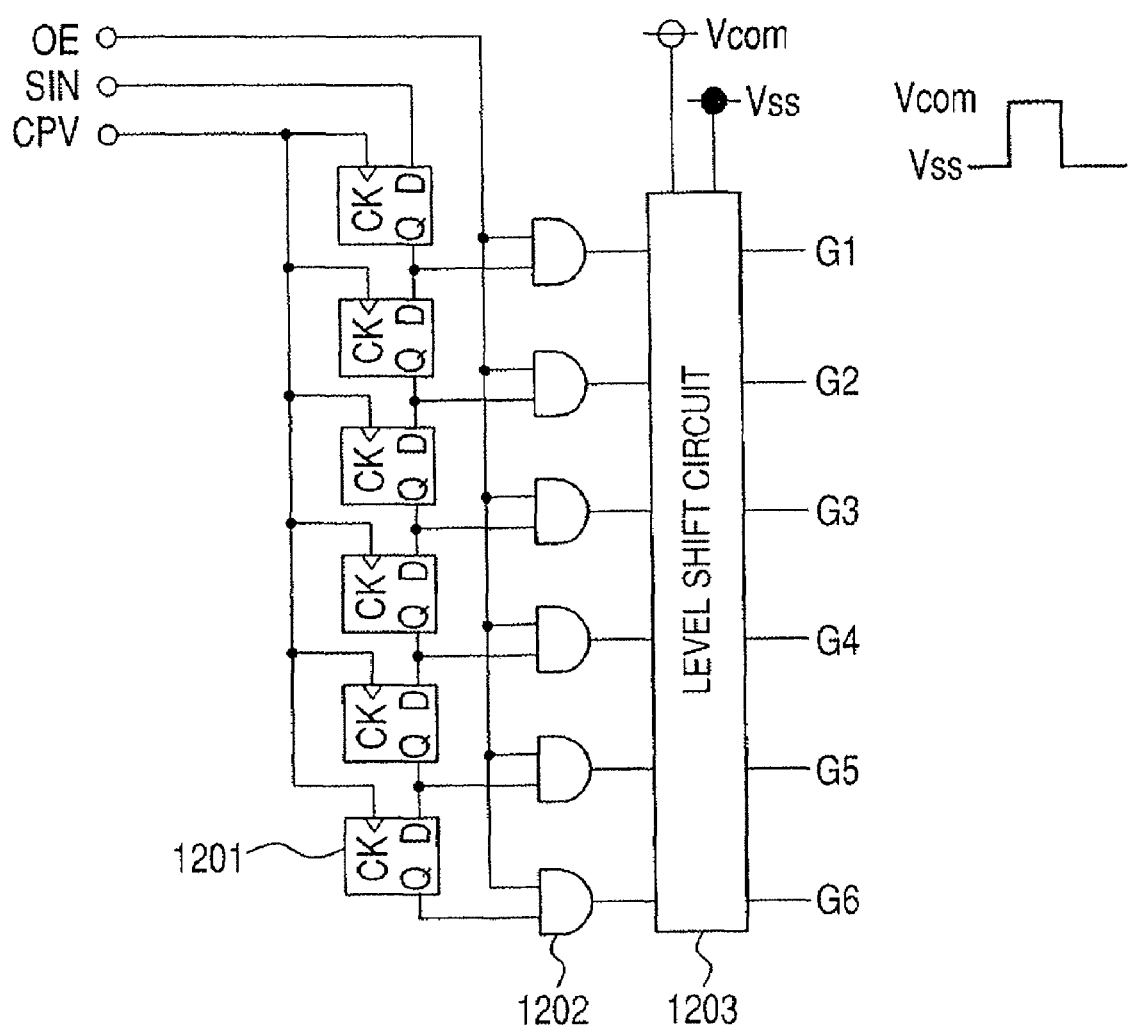
FIG. 4 illustrates an example of the circuit describing the inside of the drive circuit illustrated in FIG. 3.

FIG. 4 illustrates an example of a circuit of the inside of the drive circuit unit 1103. It corresponds to the drive circuit unit 103 shown in FIG. 3. A shift register is configured by arranging a D flip-flop 1201 and an AND element 1202 as illustrated in FIG. 4. They are controlled by three signals, that is, an OE, a SIN, and a CPV. Generally, a D flip-flip and an AND element are digital circuit, and the input/output voltage relates to a processing step for generating an element. Generally, the input/output voltage of a Hi logic is 5V system. However, with a recent request for lower power consumption and the progress of processing technology, some devices have been released as systems operated with voltages of 3.3V or less. However, generally, the switch element of the radiation detection substrate 1104 is made of amorphous silicon, and it is desired that the drive voltage is 5V or more in the current processing technology of producing amorphous silicon TFT. Therefore, a level shift circuit 1203 is provided for conversion into a drive voltage that matches the characteristic of the amorphous silicon switch element TFT.

Figure 5:
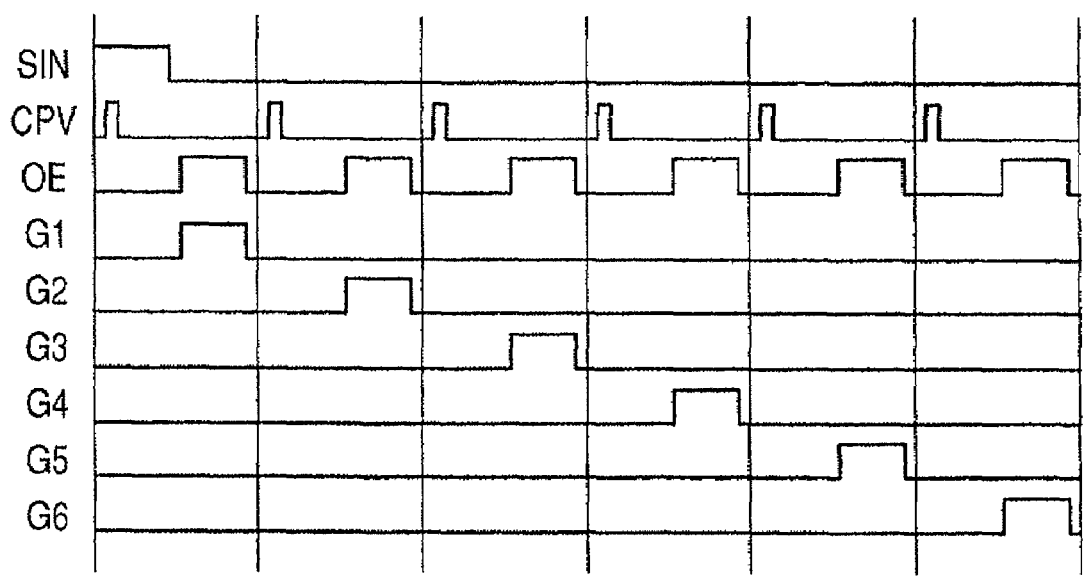
FIG. 5 is a timing chart illustrating the operation of the drive circuit illustrated in FIG. 3.

FIG. 5 is a timing chart illustrating an example of the operation of the drive circuit unit (shift register) 1103 illustrated in FIG. 3. In this example, the output of G1 to G6 is shifted stage by stage.

Figure 6:
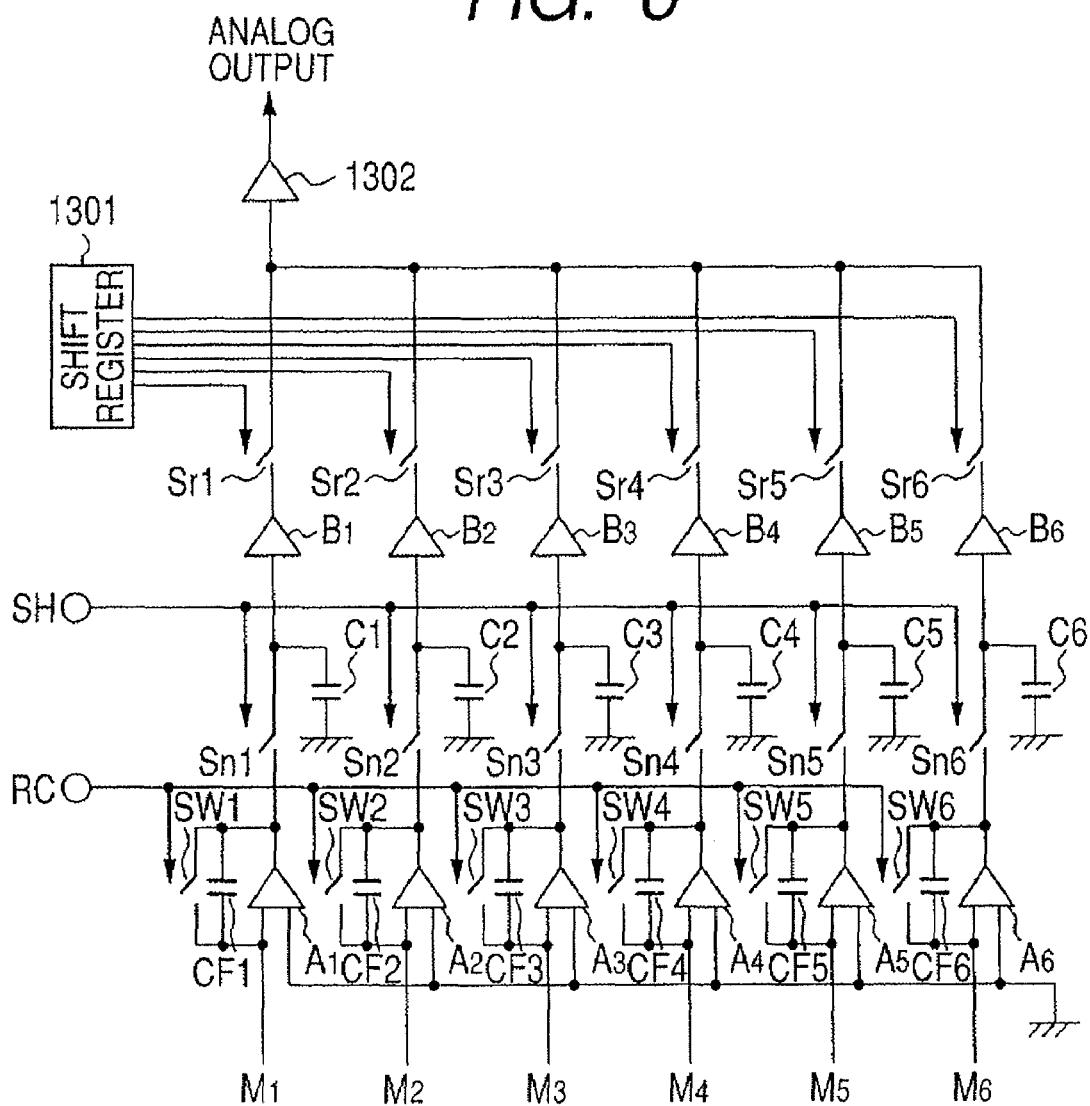
FIG. 6 illustrates an example of the circuit describing the inside of the read out circuit illustrated in FIG. 3.

FIG. 6 illustrates an example of a circuit of the inside of the read circuit unit 1102 illustrated in FIG. 3. It corresponds to the read out circuit unit 102 illustrated in FIG. 1. However, for simpler explanation, the portion of the operational amplifier AMP2 in the read out circuit unit 102 illustrated in FIG. 1 is omitted. The portion of switching between the capacitors CF1 and CF2 in the operational amplifier AMP1 is also omitted.

A1 to A6 designate operational amplifiers, and function as integrators by configuring the capacitors CF1 to CF6 as illustrated in FIG. 6. SW1 to SW6 are switch elements for resetting the integration charge of the capacitors CF1 to CF6, and reset by the control signal RC. C1 to C6 are conversion elements for sampling and holding the signals of A1 to A6, and the signals are sampled and held by turning on and off the switch elements Sn1 to Sn6. The switch elements Sn1 to Sn6 are turned on and off by the control signal SH. B1 to B6 designate buffer amplifiers for correctly transmitting the signal potential of the capacitors C1 to C6. Relating to their output, a signal from a shift register 1301 is applied from the switch Sr1 to Sr6, a parallel signal is converted into a serial signal, and output through an amplifier 1302.

Figure 7:
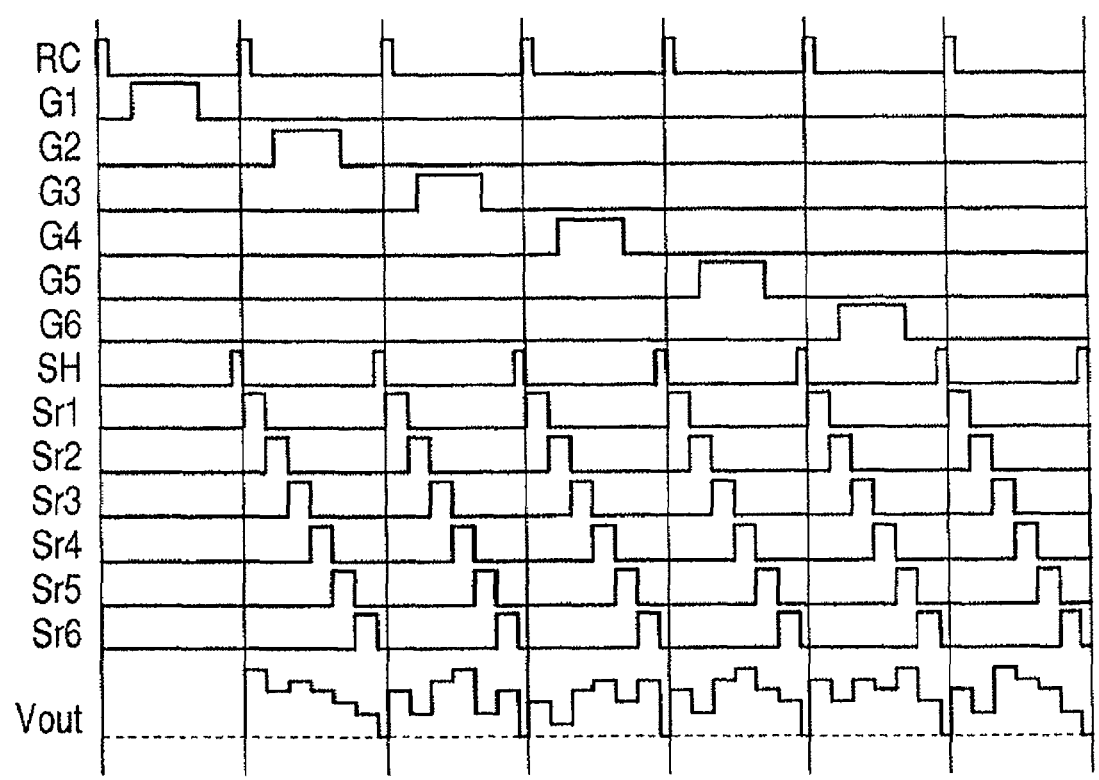
FIG. 7 is a timing chart illustrating the operation of the read out circuit shown in FIG. 6.

FIG. 7 is a timing chart illustrating an example of the operation of the read circuit unit 1102 illustrated in FIG. 6. The operation of the drive circuit unit (shift register) 1103 illustrated in FIG. 4 is also described.

First, the operation of the first row is described. The signal charge optoelectronically converted by the X-ray detection elements S1-1 to S6-1 is input to the operational amplifiers A1 to A6 of the read circuit unit 1102 through the signal wiring M1 to M6 after the switch elements T1-1 to T6-1 are turned on by the G1 signal (transfer operation) As a result, the signal charge is accumulated in the capacitors CF1 to CF6. Then, the signal SH reaches a high level (ON) and collectively transferred to the capacitor elements C1 to C6 for sampling and holding. Relating to the signals of the capacitors C1 to C6, the parallel data is rearranged into serial data in time series upon receipt of the signals Sr1 to Sr6 from the shift register 1301, and signals of one row are output (serial converting operation).

The operation for the second row is described below. According to the configuration illustrated in FIG. 6, after sampling and holding in the capacitor elements C1 to C6 according to the sampling and holding signal SH in the data of the first row, the transfer operation of the data of the second row can be performed. That is, the capacitors CF1 to CF6 are reset by the signal RC, then the transfer operation by the G2 signal is performed, and the serial conversion operation is performed. Similar operations are repeated.

In the circuit illustrated in FIG. 6, the sampling and holding circuit enables the transfer operation in the (n+1)th row and the serial conversion operation in the n-th row to be performed concurrently.

The reading time Tr for one line is roughly a total of the time (RC) for resetting the integration capacitor, and the time in which the shift register of the drive circuit unit 1103 is turned on, that is, the TFT on time (OE) and the sampling and holding time (SH).

$$Tr \approx RC + OE + SH$$

The time Tr for one line is roughly a total of the pulse widths Sr1 to Sr6 of the shift register 1301 of the read circuit unit 1102 and the sampling and holding time SH (Sr1+ Sr2+ . . . Sr6+SH).

$$Tr \approx Sr1 + Sr2 + Sr3 + Sr4 + Sr5 + Sr6 + SH$$

The reading time Tf for 1 frame is calculated as follows when there are n lines (6 lines in FIG. 3).

$Tf=Tr\times(n+1)$ (Second Mode for Embodying the Present Invention)

Figure 8:
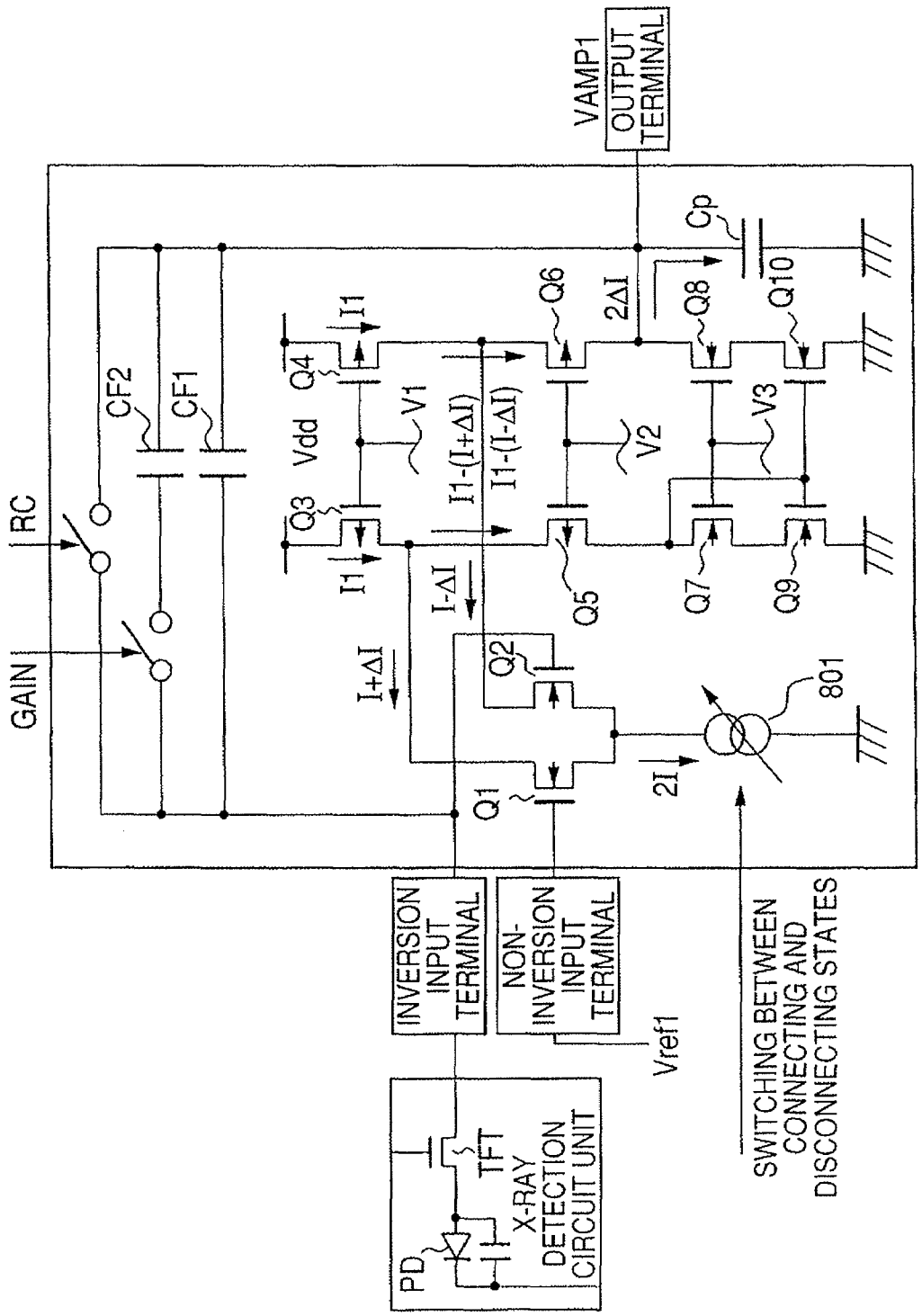
FIG. 8 illustrates the circuit of the X-ray detector in the X-ray imaging apparatus according to the second mode for embodying the present invention.

FIG. 8 illustrates an X-ray detection circuit in the X-ray imaging apparatus (radiation imaging apparatus) according to the second mode for embodying the present invention. FIG. 8 illustrates the inside of the operational amplifier of the initial stage portion of the read out circuit unit 102, and illustrates the configuration of switching the amount of current of a current source 801 connected to the differential transistor pair (Q1, Q2) of the input unit.

Although FIG. 8 illustrates the circuit of one channel, one read out circuit unit (IC chip) 102 is configured by multiple channels of, for example, 128 channels or 256 channels. Therefore, the amount of current of the current source 801 required to operate the read out circuit unit 102, that is, to operate the operational amplifier, largely affects the power consumption of the read out circuit unit 102, thereby largely influencing the heat generation from the IC chip.

In the present mode for embodying the present invention, the amount of current of the current source 801 can be switched between the connecting state radiographing in which the C arm is connected as illustrated in FIG. 19 and the non-connecting state radiographing in which the C arm is removed as illustrated in FIG. 20.

The arithmetic operation unit 106 controls the flat panel X-ray detector 11 such that the amount of current of the current source 801 of the operational amplifier during the non-connecting state radiographing can be lower than the amount of current of the current source 801 of the operational amplifier during the connecting state radiographing.

Figure 9:
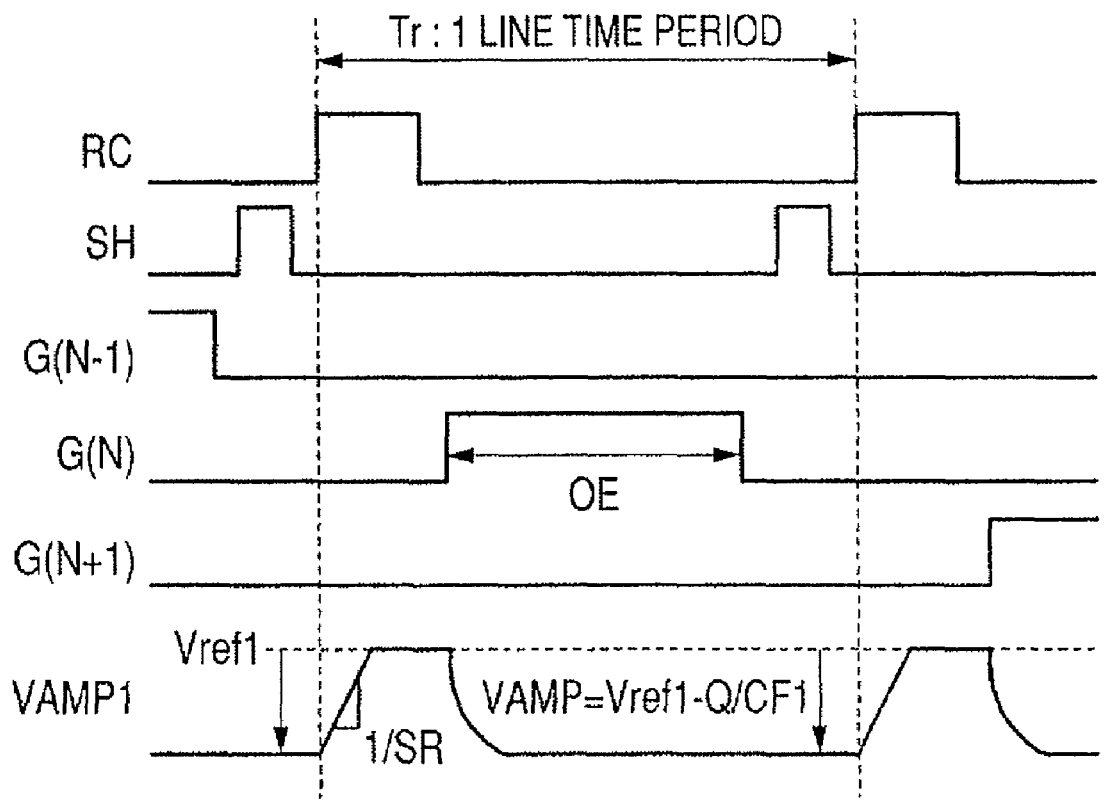
FIG. 9 is a timing chart illustrating the operation illustrated in FIG. 8.

FIG. 9 is a timing chart illustrating the operation of the circuit illustrated in FIG. 8. FIG. 9 illustrates one line (Tr) shown in FIG. 7, and also illustrates the analog output (VAMP1) of the operational amplifier AMP1.

The signal charge accumulated in the optoelectronic conversion element (X-ray detection element) PD in the radiation detection substrate 1104 is defined as Q. The integration capacitor connected to the inversion input terminal (−) of the operational amplifier AMP1 and the output terminal VAMP1 is defined as CF1. The reference potential connected to the non-inversion input terminal (+) is defined as Vref1, the output potential VAMP1 is expressed as follows.

$VAMP1=Vref1-(Q/CF1)$

However, Vref1 is reference potential, and the output voltage by the signal charge accumulated by the optoelectronic conversion element PD is defined as Q/CF1. The object of the signal RC is to reset the capacitor CF1 by setting the operational amplifier AMP1 in the buffer state, and to reset the parasitic capacitor of the signal wiring from the TFT of the radiation detection substrate 1104 connected to the inversion input terminal (−) although not illustrated in the attached drawings. After resetting the capacitor CF1 by the signal RC, the gate of the TFT is turned on for a high level time of the signal OE, and the signal charge accumulated by the optoelectronic conversion element PD of the next line is accumulated by the capacitor CF. Simultaneously, the optoelectronic conversion element PD is reset to the reference potential Vref1, thereby preparing for the accumulating operation of the next frame.

Next, the operation performed when the operational amplifier is reset illustrated in FIG. 8 is described below. Generally, when the gate potential of the transistors Q1 and Q2 of the first conductive type configuring the differential transistor pair changes, the drain currents IQ1 and IQ2 change as follows.

$IQ1=I+\Delta I$ $IQ2=I-\Delta I$

The drains of the transistors Q1 and Q2 are connected respectively to those of the transistors Q3 and Q4 of the second conductive type configuring the constant current source, and the differential current is input to the gate grounding transistors Q5 and Q6 of the second conductive type. When the current passes through the transistor Q5, it is input to the current mirror circuit configured by the transistors Q7 to Q10 of the first conductive type. By charging and discharging the phase compensation capacitor Cp due to the differential current 2ΔI between the output current, that is, the drain current Q8 of the transistor Q8, and the current IQ6 that has passed the transistor Q6, the output voltage VAMP1 can be changed.

$IQ8=I1-(I+\Delta I)$ $IQ6=I1-(I-\Delta I)$ $IQ6-IQ8=2\Delta I$

The change of the output voltage AMP1 is fed back to the gate electrode of the transistor Q2 that is an inversion input terminal (−) of an operational amplifier, and is stabilized at ΔI=0.

When the resent switch RC is turned on, the output terminal VAMP1 momentarily placed in the signal output state. Therefore, the gate potential of the transistor Q2 is lower than the gate potential of the transistor Q1 by the signal voltage Q/CF1. Therefore, the transistor Q1 is turned on, and the transistor Q2 is turned off. The change of the drain currents of the resultant transistors Q1 and Q2 is expressed as follows.

$\Delta I=I$

Therefore, the phase compensation capacitor Cp is charged by the bias current 2I of the differential transistor pair Q1 and Q2, and the time required to 1V change the output voltage VAMP1, that is, the reciprocal of the through rate SR of the operational amplifier AMP1, is expressed by the following equation.

$1/SR(sec/V)=Cp/2I$

Therefore, the reset time RC requires at least the time obtained by multiplication by the signal voltage Vsig=Q/CF1.

$RC=Vsig/SR=Q/CF1\times(Cp/2I)$

That is, to shorten the reset time RC, the value of the phase compensation capacitor Cp is reduced, or the bias current value 2I in the current source 801 is increased.

However, at the time of reset by the signal RC, the operational amplifier is a buffer amplifier. Therefore, if the value of the phase compensation capacitor is reduced, the system becomes unstable. As a result, for a stable system at the time of reset, the value of the capacitor Cp is relatively large. To charge it and raise the through rate SR, a large bias current value is required. A large bias current value is required. The bias current is a DC current to be consumed in the reading period in addition to the reset period, thereby increasing the power consumption of the entire system.

That is, to shorten the time required to read one line for a high-speed operation, the bias current is to be raised to improve the through rate. On the other hand, in this method, the power consumption increases and the heat generation also increases. Thus, the speed is traded off against the power consumption (heat generation).

In the non-connecting state radiographing in which the C arm is disconnected as illustrated in FIG. 20, the heat radiation environment of the flat panel X-ray detector is different from the environment of the connecting state radiographing in which the flat panel X-ray detector is connected to the C arm. Therefore, in the present mode for embodying the present invention, the amount of the bias current of the current source of the operational amplifier is switched to suppress the heat generation quantity.

Figure 10:
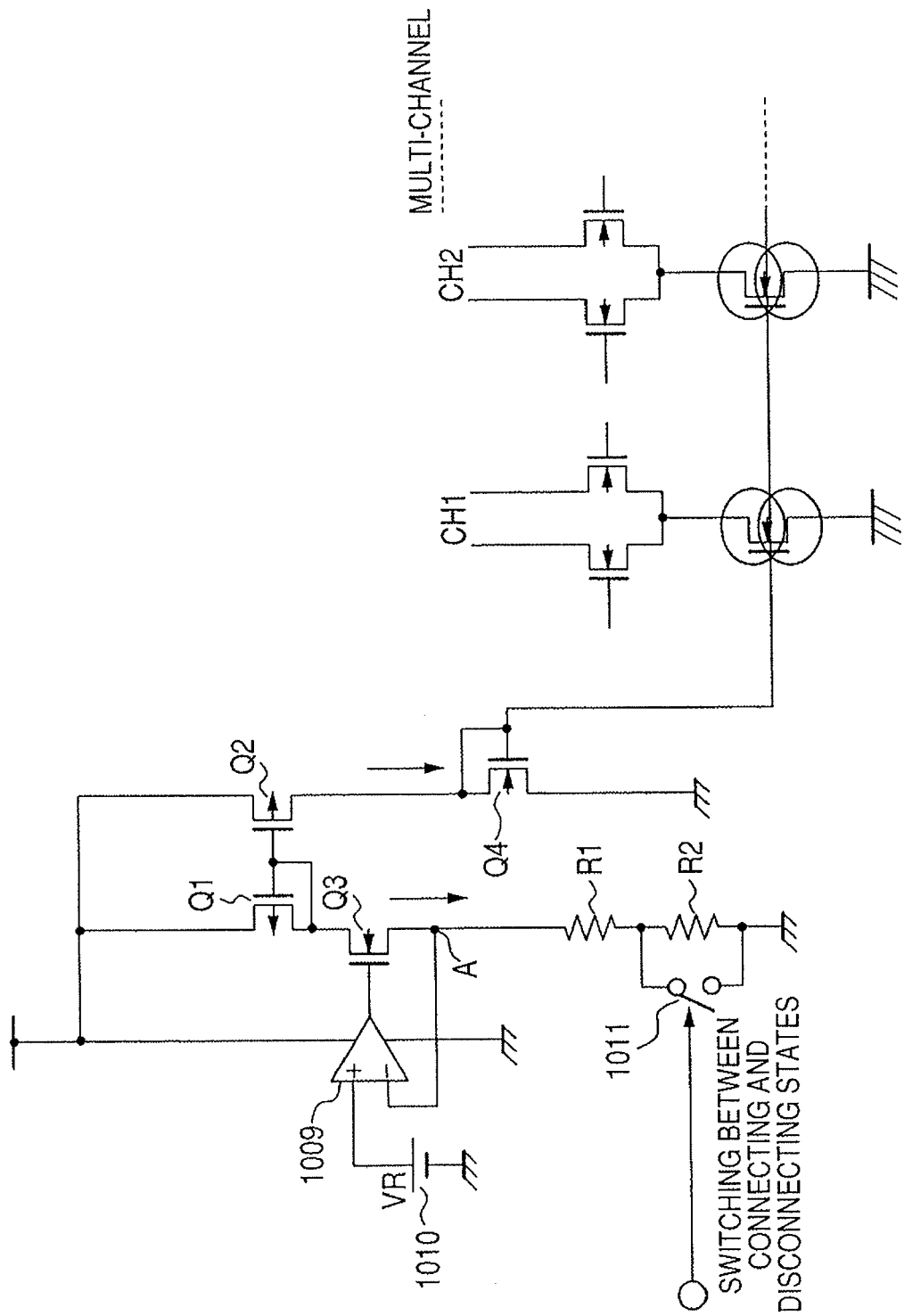
FIG. 10 illustrates an X-ray imaging apparatus according to the second mode for embodying the present invention, and illustrates a circuit for switch of operational amplifier bias currents between connecting state radiographing and non-connecting state radiographing.

FIG. 10 illustrates a circuit for switching the amount of bias current by the current source of the operational amplifier between the connecting state radiographing and the non-connecting state radiographing according to the present mode for embodying the present invention. In FIG. 10, the connection between the differential transistor pair configuring the first stage and the current sources connected to them is illustrated as an example of connecting circuits configured by multiple channels.

Reference numeral 1009 designates an operational amplifier, reference numeral 1010 designates a constant voltage source, and reference numeral 1011 designates a switch for switching between connecting state radiographing and non-connecting state radiographing.

The current Ir1 flowing through the transistors Q1 and Q3 is determined by the resistor values R1 and R2 connected to the Vr, the node A, and the GND, and calculated as the Ir1=Vr/(R1+R2) when the switch 1011 is turned off.

Since the transistors Q2 and Q4 are configured as current mirrors, the current is Ir1, and similarly the Ir1 flows through the current source connected to the differential transistor pair of the operational amplifier.

In the read out circuit unit in which 256 channels are connected to the input stage, a constant bias current of 256 times Ir1 flows. Furthermore, when not only the initial stage unit but also the next stage are configured by operational amplifiers, further double bias current flows. When the switch 1011 is turned on, and when the on-resistor of the switch is ideally zero, the resistor value connected to the node A and the GND is R1, and the current Ir2 flowing through the transistor Q1, Q2, Q3, and Q4 is Ir2=Vr/R1, and Ir2>Ir1.

In the present mode for embodying the present invention, the switch 1011 is turned on during the connecting state radiographing, and a switch 1012 is turned off during the non-connecting state radiographing, thereby switching the current consumption.

In the description relating to FIG. 10, the bias current is switched by switching the resistor value, but the voltage value VR of the constant voltage source 1010 connected to the operational amplifier 1009 can also be switched.

In the connecting state radiographing and the non-connecting state radiographing, the current consumption can be lower, that is, the heat generation quantity can be smaller, in the non-connecting state radiographing. On the other hand, since the time required at the reset time increases, the speed is lower in the non-connecting state radiographing. Since the heat generation quantity depends on the sequence of drive in each radiographing system, the resistor values R1 and R2 and the voltage value VR can be set depending on the situation.

For example, in the connecting state radiographing with the C arm connected as illustrated in FIG. 19, high-speed fluoroscopic radiographing is performed while in the non-connecting state radiographing as illustrated in FIG. 20, the still image radiographing can be performed.

Furthermore, in the non-connecting state radiographing illustrated in FIG. 20, radiographing is performed using an X-ray source fixed to the body of the C arm. However, the source is not limited to this, but another X-ray source can be used.

Also in the connecting state radiographing, high-speed fluoroscopic radiographing is performed. In the non-connecting state radiographing, the still image radiographing or the low-speed and simple fluoroscopic radiographing can also be performed.

During the non-connecting state radiographing, when the high-speed fluoroscopic radiographing equivalent to the connecting state radiographing is requested, the radiographing time can be restricted with the state of heat generation taken into account.

(Third Mode for Embodying the Present Invention)

Figure 11:
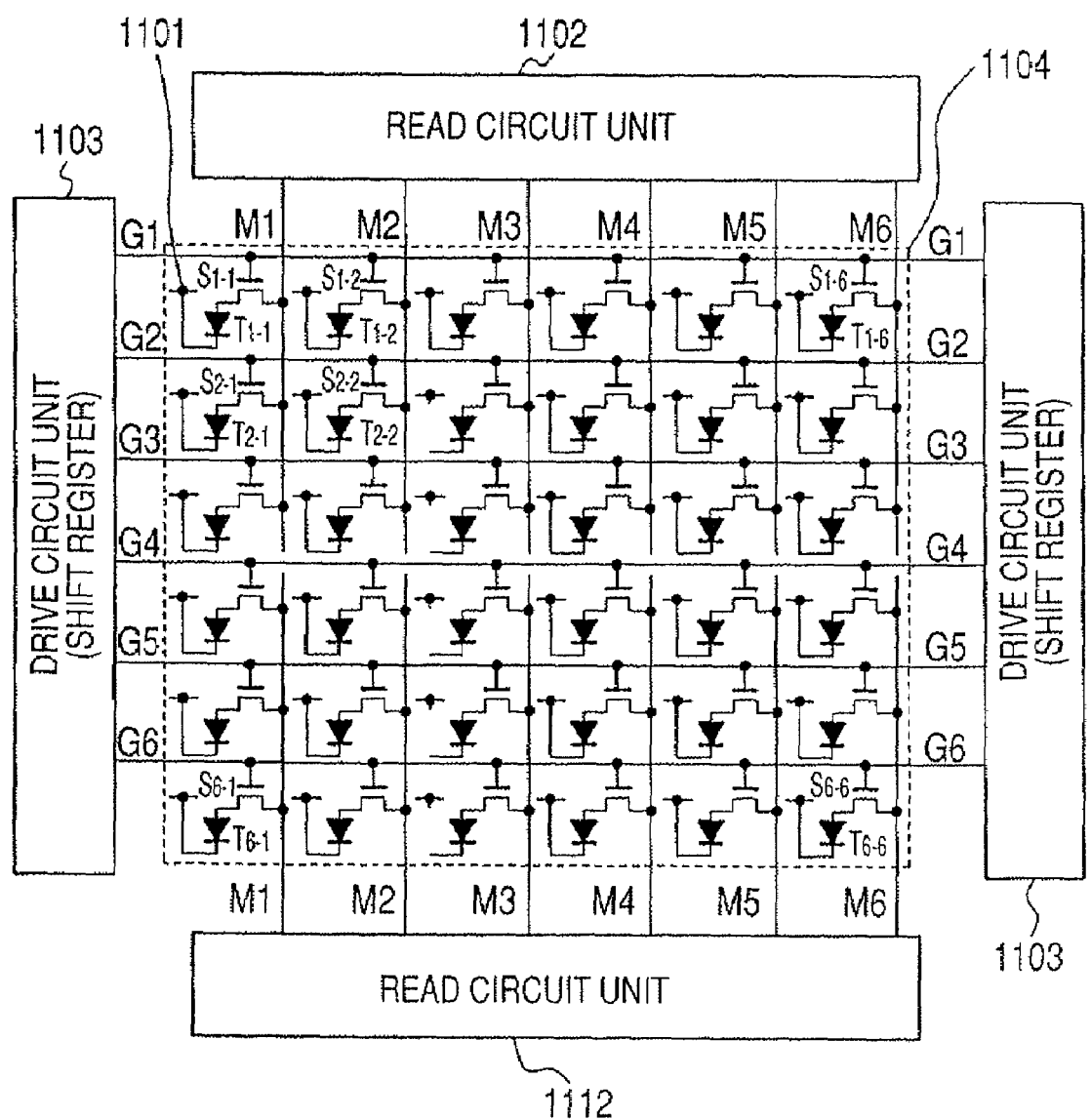
FIG. 11 illustrates the two-dimensional expression of the picture elements illustrated in FIGS. 1 and 2.

FIG. 11 illustrates the radiation detection circuit unit 1104 in the two-dimensional array using 6×6=36 picture elements as illustrated in FIG. 3. The difference from FIG. 3 is that the signal wiring (vertical wiring in FIG. 11) M1 to M6 connected to the TFT are separated at the center, and the read out circuit unit (1102, 1112) are directed upward and downward. In addition, the drive circuit unit 103 for drive of the gate wiring (horizontal wiring in FIG. 11) G1 to G6 of the TFT is provided left and right. The gate wiring G1 to G6 are not separated at the center.

Thus, by separating the signal wiring M1 to M6 at the center, for example, the row G1 and the tow G4 can be simultaneously driven. Next, since the row G2 and the row G5 can be simultaneously driven and the row G3 and the row G6 can be simultaneously driven, the reading time for one frame can be about half the time illustrated in FIG. 3. That is a higher operation can be realized. By connecting the drive circuit unit 1103 at right and left, the delay of the gate drive pulse and the deformation of a waveform caused by the wiring resistance of the gate wiring G1 to G6 and the wiring capacitor can be prevented or reduced. Since the deformation of a waveform of the gate wiring G1 to G6 causes variances in offset output waveform, it is desired that the drive circuit units 1103 are simultaneously driven from both right and left as illustrated in FIG. 11.

On the other hand, as compared with FIG. 3, in the circuit configuration in FIG. 11, there have to be a double number of read out circuit units and driving circuit units respectively.

For example, to medically radiograph a chest portion of a person, for a 41 cm×41 cm light receiving area, the resolution of 160 µm pitches is requested. For a 41 cm×41 cm light receiving area with 160 µm pitches, the number of picture elements are 2560×2560=about 6.55 million picture elements.

Figure 12:
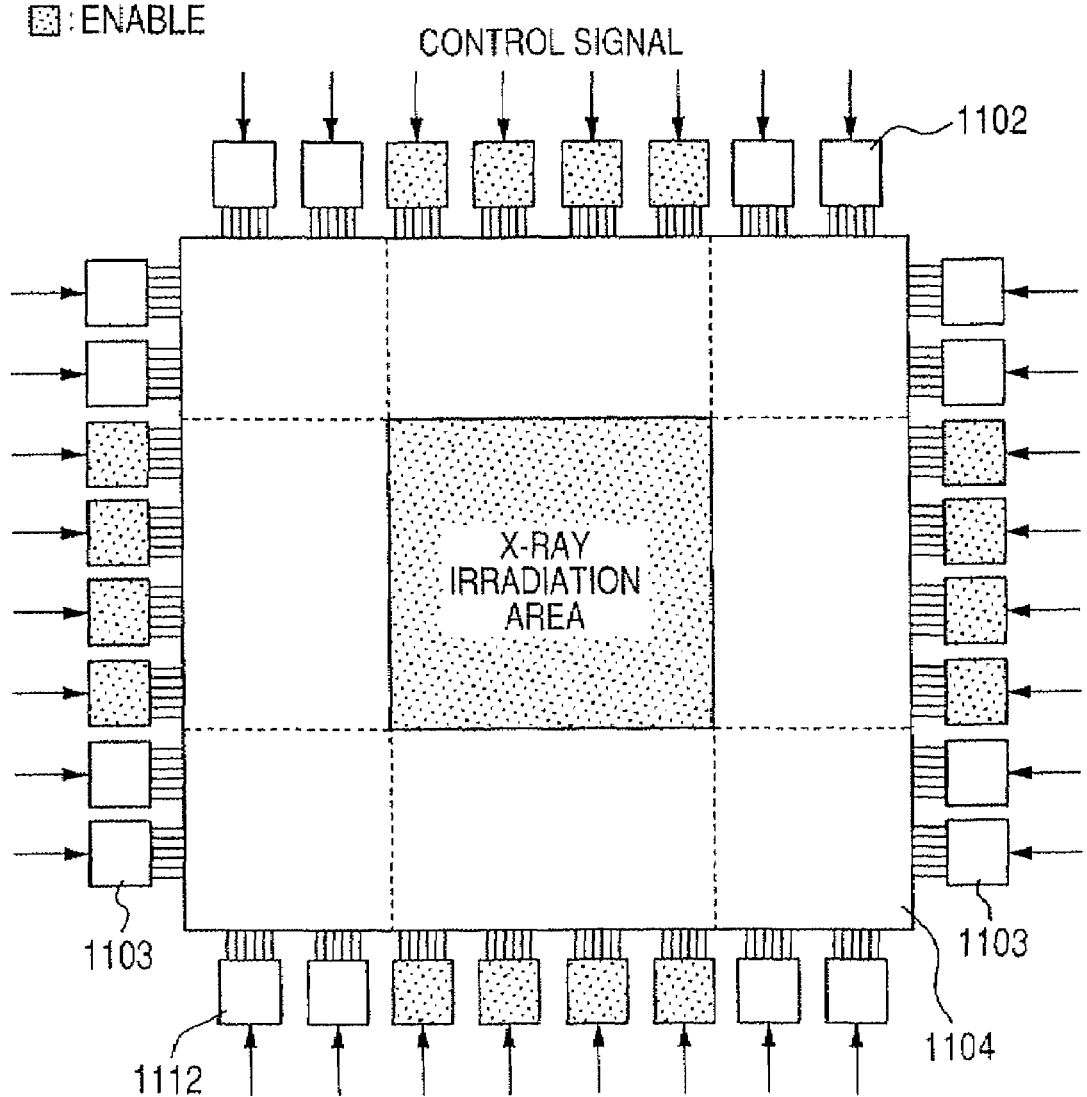
FIG. 12 illustrates the state (non-connecting state radiographing) of the operation of the X-ray detector according to the third mode for embodying the present invention.

As an example, when each IC of the read circuit units 1102 and 1112 is configured by 320 channels, the required number of read circuit units (IC) 1102 and 1112 is, in the case shown in FIG. 11, a total of 16 including the upper and lower units. When the IC of the drive circuit unit 1103 is configured by 320 channels per unit, the required number of drive circuit units (IC) 1103 is 16 including the left and right units. FIG. 12 illustrates the outline of the installed state of the example.

FIG. 12 illustrates an example of the operation of the flat panel X-ray detector in the non-connecting state radiographing according to the third mode for embodying the present invention. The present mode for embodying the present invention drives the entire IC in the connecting state radiographing when the C arm is connected. In the non-connecting state radiographing in which the C arm is disconnected, only the corresponding read circuit units 1102, 1112, and drive circuit unit 1103 are operated (enabled) depending on the X-ray irradiation area (irradiation field). The read circuit units 1102 and 1112 and the drive circuit unit 1103 other than the X-ray irradiation area are not operated (disabled). When the boundary of the X-ray irradiation area is in the channels of the read circuit units 1102 and 1112, the read circuit is "enabled". When the boundary of the X-ray irradiation area is in the channels of the drive circuit unit 1103, the drive circuit is "enabled"

The switch between "enable" and "disable" is performed according to a control signal input to each IC. When the IC is set as "disabled", the power consumption is much lower and the heat generation quantity is smaller than the IC set as "enabled".

The X-ray irradiation area is selected by a collimator provided near the emission unit of X-ray source to automatically control the collimator, or to manually determine it.

The read circuit units 1102 and 1112, and the drive circuit unit 1103 can be selected by, for example, once scanning the radiation detection circuit unit 1104 in advance, recognizing the irradiation field from the data of the read circuit units 1102 and 1112, and reflecting the result by the subsequent radiographing (in the case of moving image radiographing).

Otherwise, a radiographing engineer can manually determine the irradiation field in advance, and depending on the determination, the read circuit units 1102 and 1112 and the drive circuit unit 1103 can be selected.

Figure 13:
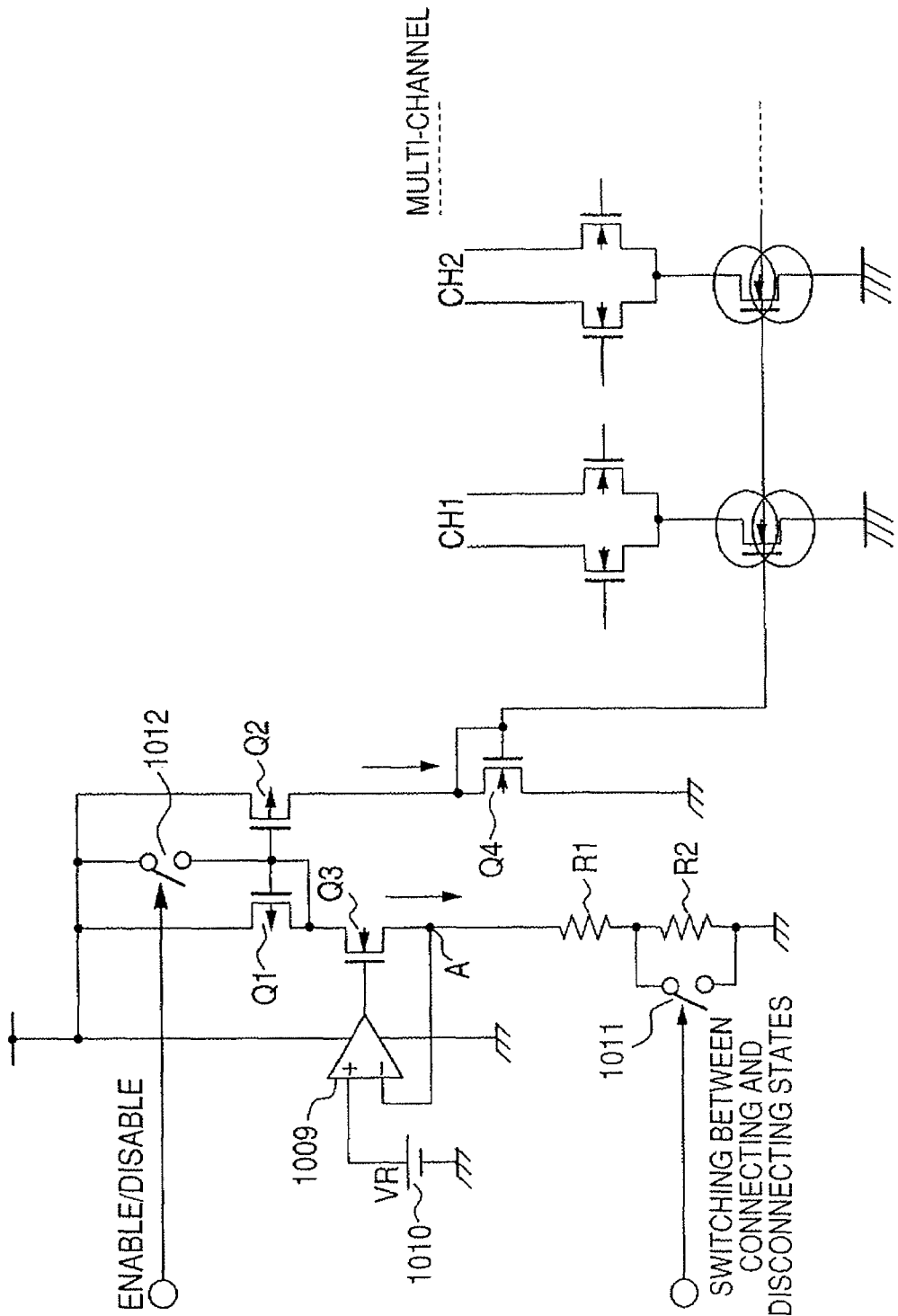
FIG. 13 illustrates the read out circuit unit of the flat panel X-ray detector according to the third mode for embodying the present invention, and the circuit unit for switch between "enable" and "disable".

FIG. 13 illustrates an example of the circuit of switching "enable" and "disable" in the read circuit units 1102 and 1112 of the flat panel X-ray detector according to the third mode for embodying the present invention. FIG. 13 is different from FIG. 10 in that it includes a switch 1012 between the gates of the transistors Q1 and Q2 and the power supply. When the switch 1012 is turned on, the PMOS (Q2) is turned off, no current flows to the current source connected to the differential transistor pair of each channel, and no operation of the operational amplifier is performed. That is, the power consumption becomes extremely low, and the heat generation is suppressed.

In FIG. 12, the control signal is provided for each IC. However, since the boundary of the X-ray irradiation field can be in the channel, a plurality of control lines can be provided in each IC for more efficient control.

FIG. 13 illustrates the control of the current source of the operational amplifier at the initial stage. However, when operational amplifiers are cascaded at the second and third stages, similar connection can be made for control. In this case, the current sources of 320 ch×3=960 operational amplifiers are stopped per chip, thereby largely suppressing the power consumption, and then considerably reducing the heat generation quantity.

In the non-connecting state radiographing, the arithmetic operation unit 106 controls the flat panel X-ray detector 11 to operate the read circuit units 1102 and 1112 and the drive circuit unit 1103 for the X-ray (radiation) irradiation field, but to set the read circuit units 1102 and 1112 and the drive circuit unit 1103 for a field outside the X-ray (radiation) irradiation field at a non-operating state or at a state of reduced current consumption.

(Fourth Mode for Embodying the Present Invention)

Figure 14:
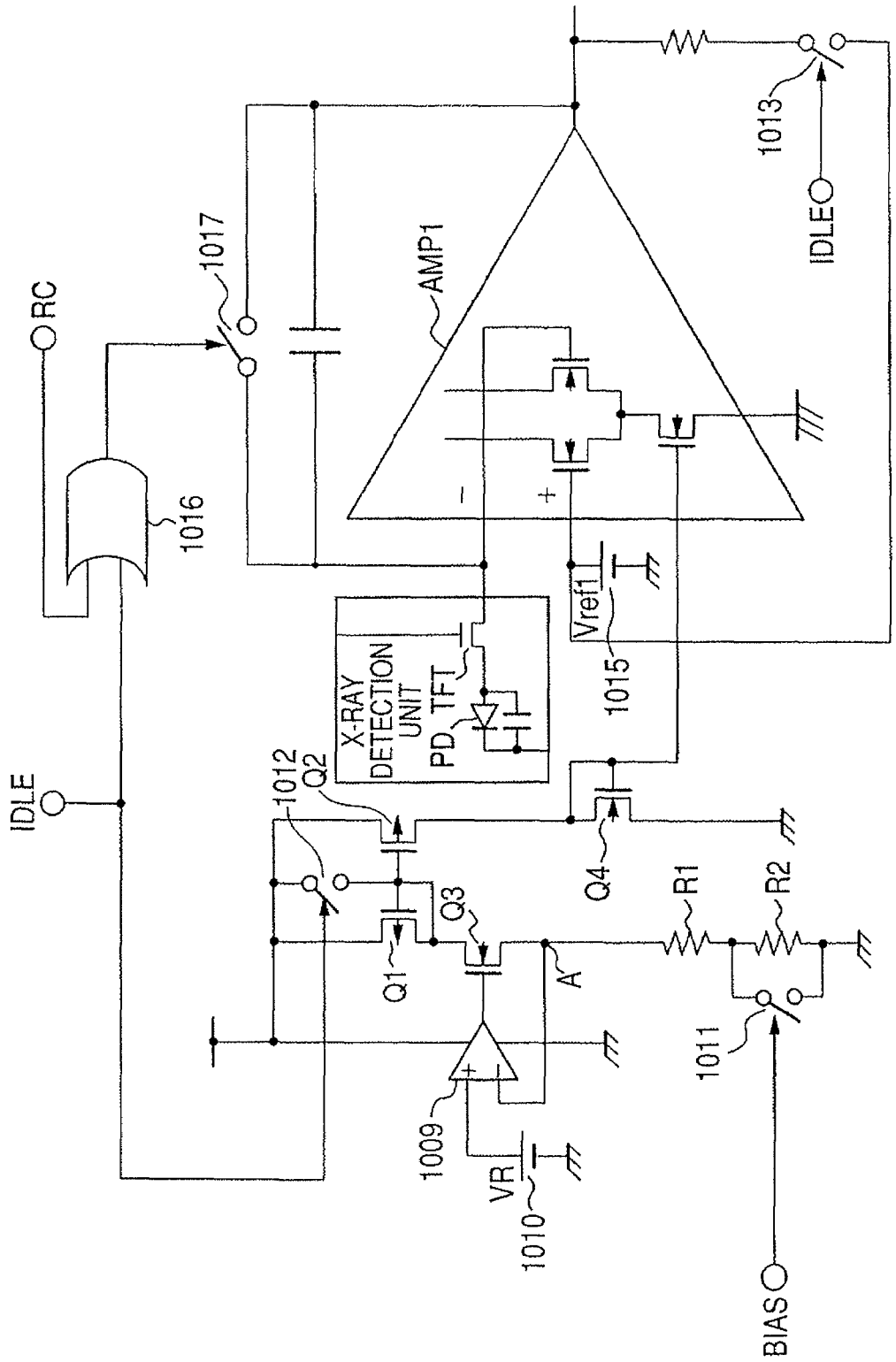
FIG. 14 illustrates the circuit of the flat panel X-ray detector according to the fourth mode for embodying the present invention.

FIG. 14 illustrates the circuit of the picture elements according to the fourth mode for embodying the present invention. In FIG. 14, the control terminal for cutting off (disable) a bias current of an operational amplifier described by referring to the third mode for embodying the present invention is assigned a terminal name "IDLE". Furthermore, the control terminal for switching the amount of bias current of an operational amplifier described by referring to the second mode for embodying the present invention is assigned a terminal name "BIAS". Signal wiring is connected from the picture elements to the inversion input terminal of the operational amplifier (AMP1). The non-inversion input terminal of the operational amplifier (AMP1) is assigned the potential of Vref1 by a reference potential 1015. The switch 1013 is connected to the output terminal of the operational amplifier (AMP1) through a protective resistor so that the signal IDLE controls the output terminal to be connected to the Vref1. That is, when the signal IDLE is turned on, an OR circuit 1016 turns on the switch 1017, the control of the signal RC cannot work, and the signal wiring from the inversion input terminal (−) of an operational amplifier, that is, the flat panel X-ray detector (X-ray detection substrate), is biased to the Vref1.

In other words, the output terminal and the inversion input terminal can be equivalent in potential without operating the operational amplifier AMP1 in the buffer state, which is advantageous in power consumption.

When an X-ray detection element (optoelectronic conversion element) is configured by a material such as amorphous silicon and the like, the element immediately after power-up is not stable in dark current, and it is necessary to perform a pseudo-drive for a while. The pseudo-drive is referred to as idling. Operating an operational amplifier (enable) in the idling period consumes electric power and heat generation occurs.

Therefore, in the period, the flat panel X-ray detector performs the idling operation, and it is desired that the operational amplifier is in the "disabled" state. Thus, the total power consumption for the radiographing operation can be reduced. In the present mode for embodying the present invention, the operational amplifier is placed in the "disabled" state according to the signal IDLE, and the bias of the Vref1 is applied to the signal wiring of the flat panel X-ray detector through the switch 1017 from the output terminal of the operational amplifier. Thus, the idling operation can be performed by supplying the gate voltage of the TFT and the bias of the photodiode.

Figure 15:
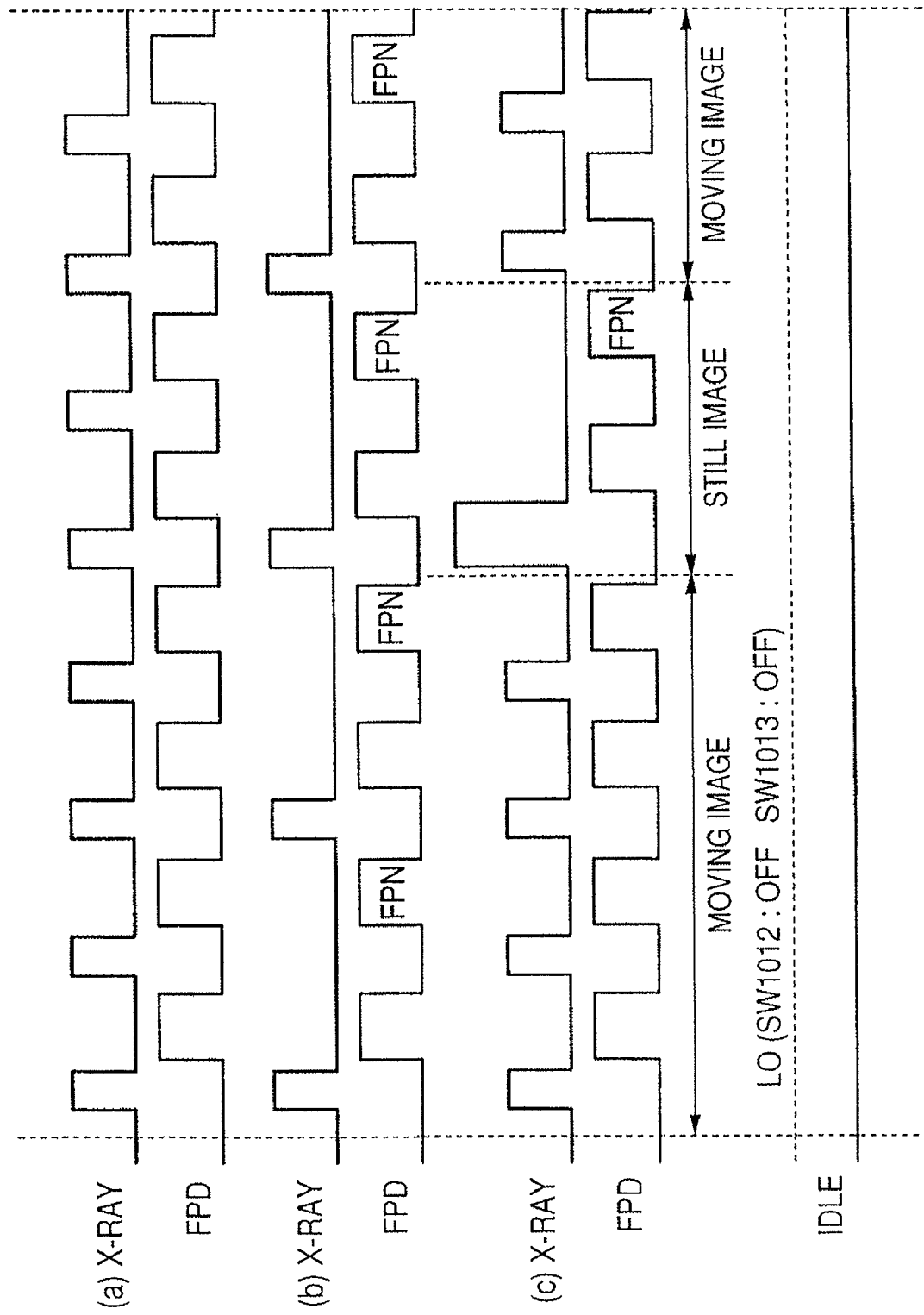
FIG. 15 is a timing chart illustrating the operation (connecting state radiographing) according to the fourth mode for embodying the present invention.

FIG. 15 is a timing chart illustrating the operation according to the present mode for embodying the present invention, and illustrates the timing in connecting state radiographing. The operation of the X-ray detector is represented by "FPD".

Part (a) of FIG. 15 illustrates an example in which X-ray pulses are continuously emitted, and one frame of image data is read from the FPD while the X-rays are not emitted. The radiographing is an example of fluoroscopic radiographing.

Part (b) of FIG. 15 also illustrates an example of fluoroscopic radiographing. It illustrates an example of reading one frame of image data and one frame of FPN (fixed pattern noise) data from an FPD while X-rays are not being emitted in the period when pulses of X-rays are continuously emitted. By subtracting the FPD from the image data, the fixed pattern noise of the flat panel X-ray detector and the afterimage components of optoelectronic conversion element are removed. Part (b) of FIG. 15 indicates a half reduced frame rate as compared with part (a) of FIG. 15.

Part (c) of FIG. 15 illustrates an example of inserting still image radiographing while performing fluoroscopic radiographing illustrated by part (a) of FIG. 15. Since still image radiographing data is commonly used in a detail diagnosis, more X-rays are emitted than the X-rays emitted during fluoroscopic radiographing. In the drawing, FPN data is collected in the still image radiographing while the FPN data is not collected in the fluoroscopic radiographing. In part (c) of FIG. 15, the fluoroscopic radiographing is performed again after the still image radiographing, but the process can be terminated by the still image radiographing.

In parts (a), (b), and (c) of FIG. 15, the IDLE terminal is in the "low level (Lo)" in any period, that is, the switch 1012 and the switch 1013 are turned off, but the operational amplifier AMP1 is operating in the "enabled" state.

Figure 16:
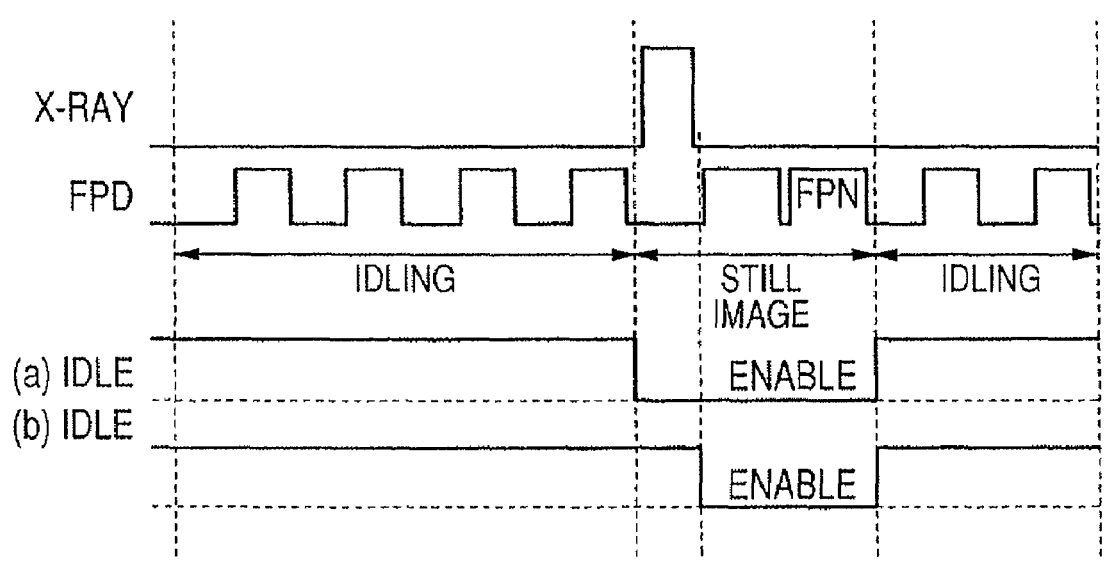
FIG. 16 is a timing chart illustrating the operation (non-connecting state radiographing) according to the fourth mode for embodying the present invention.

FIG. 16 is a timing chart illustrating the operation according to the present mode for embodying the present invention, and illustrates the timing in the non-connecting state radiographing. FIG. 16 describes the sequence of the still image radiographing.

FIG. 16 illustrates the "disabled" state in which the bias current of an operational amplifier is cut off by turning the IDLE terminal to the "high level (Hi)" (on) until the still image radiographing is performed to reduce the power consumption and suppress heat generation. However, in the period, although not illustrated in the attached drawings, a bias is applied to the drive of the TFT and the sensor, and the X-ray detection circuit is placed in the idling operation state.

When a request for the still image radiographing is issued, pulses of X-rays are emitted, the image data is read, and the FPN data is further read again. Back to the idling operation, the still image radiographing is performed on the second piece of data.

In part (a) of FIG. 16, the "IDLE" signal is switched to the point before the irradiation of X-rays. In part (b) of FIG. 16, the "IDLE" signal is switched to the point after the irradiation, that is, the point immediately before the reading operation. Either case is accepted, but the heat generation can be more efficiently reduced in part (b) of FIG. 16.

In FIG. 14, only one channel is expressed for convenience of the layout on the sheet, but it is obvious that a multi-channel configuration as illustrated in FIG. 13 can be accepted.

The flat panel X-ray detector 11 can perform moving image radiographing and still image radiographing in the connecting state radiographing, and the idling drive and the still image radiographing in the non-connecting state radiographing.

(Fifth Mode for Embodying the Present Invention)

Figure 17:
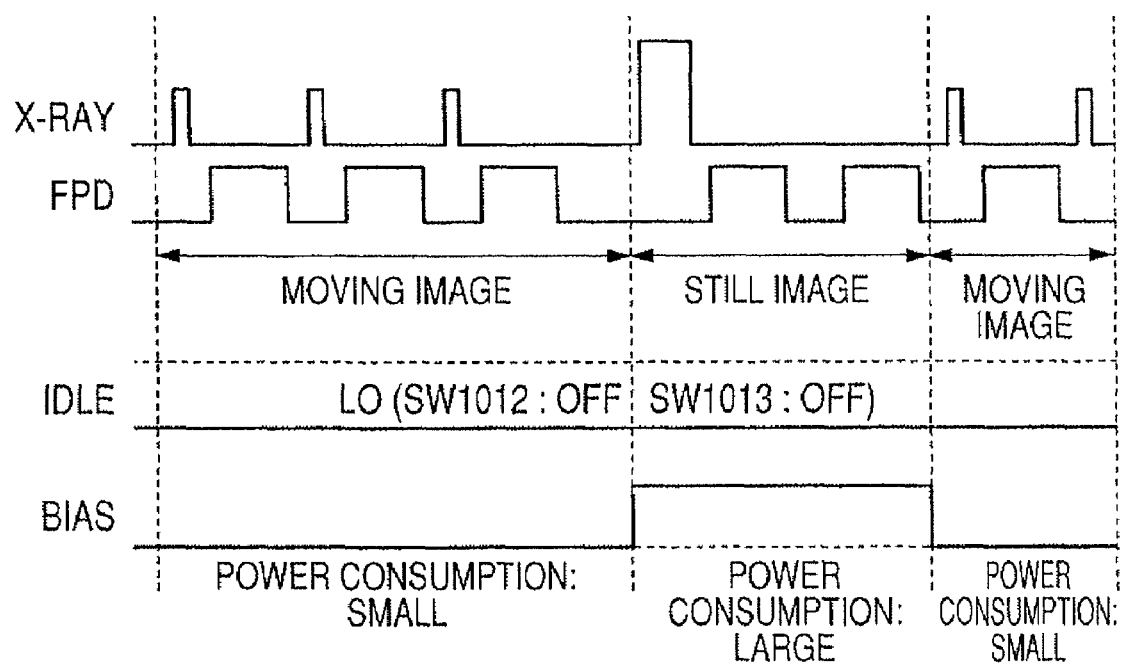
FIG. 17 is a timing chart illustrating the operation (non-connecting state radiographing) according to the fifth mode for embodying the present invention.

FIG. 17 is a timing chart illustrating the operation according to the present mode for embodying the present invention, and shows a timing during non-connecting state radiographing. Although FIG. 16 illustrates only the example of still image radiographing, FIG. 17 illustrates combination radiographing of the fluoroscopic radiographing and the still image radiographing. In the fluoroscopic radiographing, a BIAS terminal is placed in the "Lo" (off) state, to reduce the power consumption of the operational amplifier, thereby suppressing the heat generation. However, in this case, the BIAS terminal is somewhat disadvantageous in respect of speed as compared with the BIAS terminal in the "Hi" state. Therefore, high-speed fluoroscopic radiographing cannot be performed as compared with the case of the BIAS terminal in the "Lo" state. When there is a request for the still image radiographing, the X-rays for still images are emitted, a reading operation for one frame of still images is performed, and the reading operation of the FPN is further performed. In FIG. 17, the BIAS terminal is placed in the "Hi" state in this period.

The random noise of a transistor depends on the bias current passing through the differential transistor pair at the input stage of an operational amplifier. Generally, by passing a strong current, the conductance of the differential transistor pair at the input unit is reduced, thereby suppressing the noise. In the present mode for embodying the present invention, since radiographed still image is used for a diagnosis, the BIAS terminal is placed in the "Hi" state in the still image radiographing.

However, when the amount of X-ray irradiation can be set large, or when the S/N ratio is not so strict, it is not necessary to strictly set the BIAS terminal in the "Hi" state. That is, the selection can be made depending on the purpose of radiographing and diagnosis.

(Sixth Mode for Embodying the Present Invention)

Figure 18A:
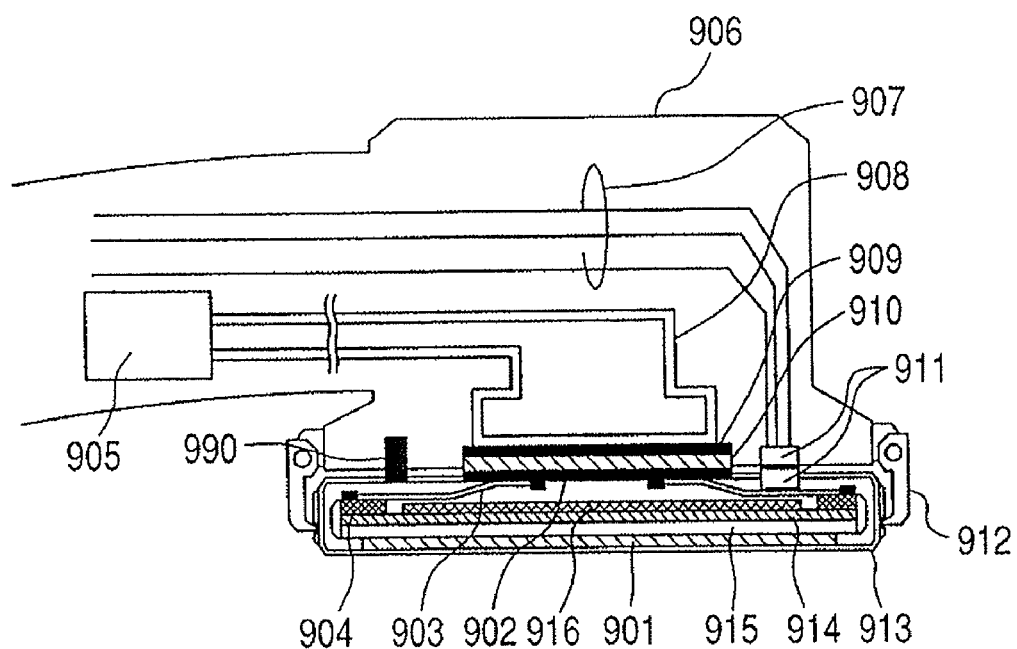
FIG. 18 illustrates the X-ray imaging apparatus according to the sixth mode for embodying the present invention, and illustrates the structure of the C arm and the X-ray detector.
Figure 18B:
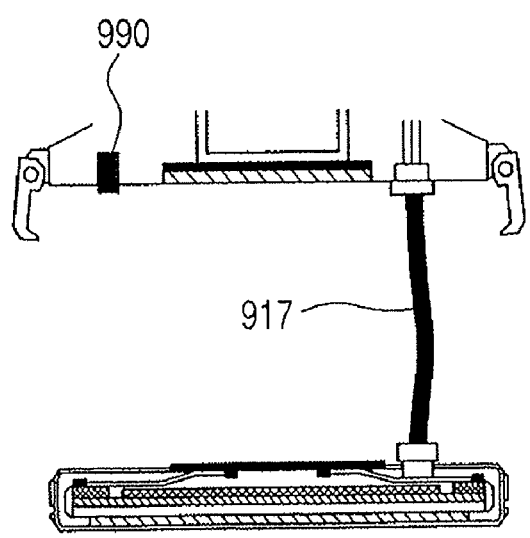

FIG. 18 illustrates the outline of the X-ray imaging apparatus according to the sixth mode for embodying the present invention. It indicates the structure of the C arm and the X-ray detector. The apparatus includes a phosphor 901, a heat dissipation plate 902, a heat pipe 903, a read circuit 904, a heat exchange 905, a C arm 906, a signal-power supply cable 907, a heat pipe 908, a heat dissipation plate 909, a heat conductive sheet 910, a connector 911, a fixing hook 912, a flat panel X-ray detector 913, a support substrate 914, a two-dimensional sensor 915, a system substrate 916, an extension cable 917, and a connection state detection unit 990.

The flat panel X-ray detector 913 according to the present mode for embodying the present invention is a two-dimensional sensor having the circuit configuration shown in FIGS. 3, 11, and 12, and on the optical incident plane the phosphor 901 is provided for converting X-rays into visible light. Reference numeral 904 designates a read circuit. No drive circuit is illustrated in FIG. 9. The components are connected to the support substrate 914.

Fixed to the support substrate 914 are the power supply control unit for controlling and supplying power such as an AD converter, a driving circuit unit (not shown in the attached drawings), a timing generation unit, a radiation detection circuit, a driving circuit unit, a read out circuit unit, etc. and a system substrate such as an arithmetic operation unit provided with memory, a CPU, etc. The AD converter A/D converts a signal output from the read out circuit unit. The timing generation unit assigns timing to the read circuit. There is one system substrate 916 illustrated in FIG. 18, but a plurality of substrates can be provided.

In the present mode for embodying the present invention, the flat panel X-ray detector 913 is provided with the heat dissipation plate 902. The heat pipe 903 is connected to the heat dissipation plate 902 so that the heat generated by the read circuit 904 and the like is transmitted.

The C arm 906 is provided with the heat dissipation plate 909 and the heat conductive sheet 910 as with the above-mentioned flat panel X-ray detector 913. In the state in which the C arm 906 and the flat panel X-ray detector 913 are combined, the heat dissipation plate 902 of the flat panel X-ray detector 913 is thermally connected to the heat dissipation plate 909 of the C arm 906 through the heat conductive sheet 910.

The C arm 906 is provided with the heat pipe 908 and the heat exchange 905 for externally dissipating the heat of the heat dissipation plate 909, and the heat transmitted from inside the flat panel X-ray detector 913 can be radiated externally. The flat panel X-ray detector 913 has heat dissipation transmission unit for transmitting and dissipating the generated heat to the C arm 906 when the detector is connected to the C arm 906.

The heat pipe 908 is generally referred to as a heat conductive system on the basis of a reciprocal change between vaporization and liquefaction of a liquid sealed inside and a capillary phenomenon. The thermal conductivity of the heat pipe 908 is considerably high, and the heat can be efficiently transmitted.

The heat pipe 908 has a high degree of freedom, has no moving portion, and requires no maintenance. Therefore, it is applicable to a device requiring high reliability such as medical equipment.

The materials of the heat dissipation plates 902 and 909 in the present mode for embodying the present invention can be metal of high thermal conductivity such as copper, aluminum, etc.

The heat conductive sheet 910 is a sheet of silicone rubber and an acrylic rubber of high thermal conductivity. In connecting heat diffusion plates of metal, the air layer between the plates prevents the heat from being efficiently conducted. However, the heat conductive sheet 910 avoids the defect. The heat conductive sheet 910 is fixed to the heat dissipation plate 909 on the C arm 906.

The electrical connection between the C arm 906 and the flat panel X-ray detector 913 according to the present mode for embodying the present invention is made simultaneously when the flat panel X-ray detector 913 is fixed to the C arm 906.

The electrical connection between the radiographing system including the C arm 906 and the flat panel X-ray detector 913 is made by the connector 911. Necessary power supply and electrical signal for driving the flat panel X-ray detector 913 are supplied from the C arm 906 through the connector 911, and the image data and the status signal of the system are output from the flat panel X-ray detector 913 to the C arm 906.

Part (b) of FIG. 18 illustrates the state in which the flat panel X-ray detector 913 is separated from the C arm 906. When the flat panel X-ray detector 913 is separated from the C arm 906, the radiographing using the flat panel X-ray detector 913 can be performed by connecting the extension cable 917 to the connector 911.

The connection state detection unit (connection detection unit) 990 in FIG. 18 detects the time (non-connecting state) when the flat panel X-ray detector 913 is connected to the C arm 906 and when it is removed from the C arm 906. Whether it is a connected state or a non-connected state is detected, and according to a resultant signal, the heat generation quantity of the X-ray imaging unit is differentiated.

Figure 22:
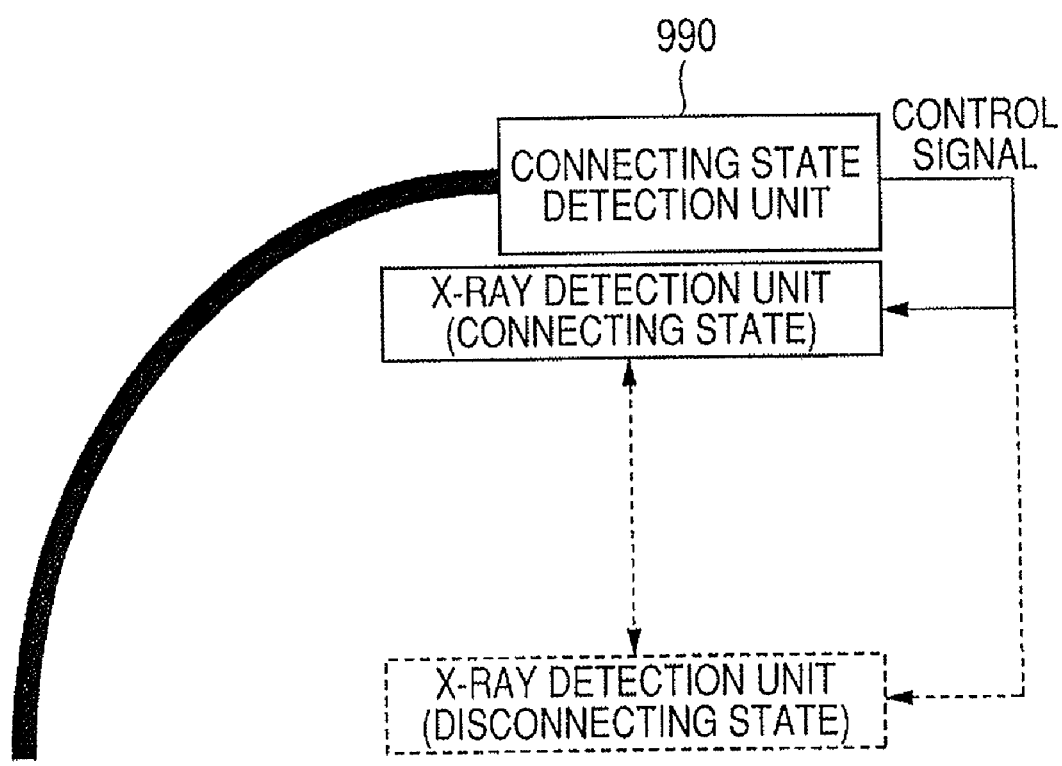
FIG. 22 illustrates the outline of detecting the connection state by the connection detection unit provided at the C arm and controlling the X-ray imaging unit according to the control signal.

FIG. 22 illustrates the outline of detecting the connected state by the connection state detection unit 990 provided for the C arm 906, and controlling the X-ray imaging unit according to the control signal.

According to the control signal from the connection state detection unit 990, a feedback is applied to the arithmetic operation unit 106 in FIGS. 1 and 2, and according to the control signal from the arithmetic operation unit 106 to the power supply control unit 104, the voltages Vs, Vcom, Vdd, Vref1, etc. are controlled, and the heat generation quantity is controlled.

Additionally, according to the control signal from the connection state detection unit 990, in FIG. 8, the current source 801 is controlled, thereby changing the heat generation quantity.

Furthermore, according to the control signal from the connection state detection unit 990, the heat generation quantity can be changed by controlling the switch 1011 as illustrated in FIGS. 11 and 13.

According to the control signal from the connection state detection unit 990, the heat generation quantity can be changed by changing the state (enabled/disabled) of each of the read circuit and the drive circuit as illustrated in FIG. 12. Although not illustrated in FIG. 12, the method of selecting the states can be easily attained by fully using the present digital technology.

Also according to the control signal from the connection state detection unit 990, as illustrated in FIGS. 15, 16, and 17, the heat generation quantity can be changed by changing the IDLE signal and the BIAS signal. Although not illustrated in the attached drawings, the method of generating the IDLE signal and the BIAS signal can be easily attained by fully using the present digital technology.

Figure 21A:
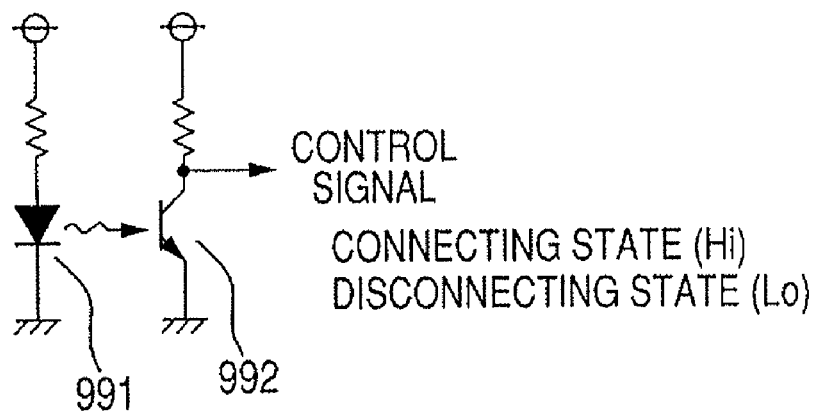
FIGS. 21A and 21B illustrate examples of the connection detection unit.
Figure 21B:
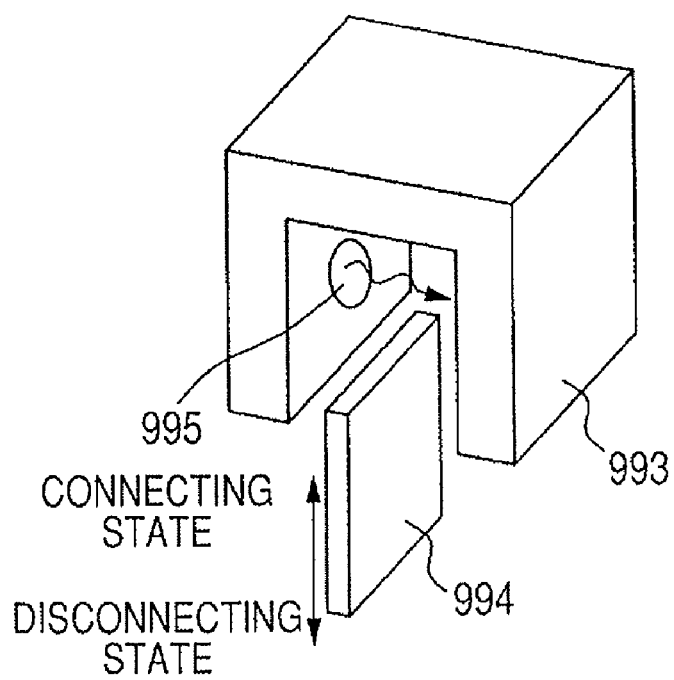

FIGS. 21A and 21B illustrate examples of the connection state detection unit 990. FIG. 21A illustrates an electric circuit, and FIG. 21B illustrates the mechanical concept.

A light emission diode (LED) 991 is turned on when the light from the light emission diode 991 is emitted to the base portion (light receiving portion) of a phototransistor 992, and the control signal enters the "Lo" level. When the light of the light emission diode 991 is not emitted to the light receiving portion of the phototransistor 992, the diode is turned off, and the control signal enters the "Hi" state.

A member 993 has an embedded electric circuit illustrated by FIG. 21A. The light of the LED that has passed a window 995 is input to the phototransistor unit (not illustrated in FIGS. 21A and 21B) through the window (not illustrated in FIGS. 21A and 21B) provided in the opposite portion. A shading member 994 is a shading member for cutting off the light between the LED and the phototransistor when the X-ray imaging unit is connected to the C arm 906, and allowing the light of the LED to be emitted to the phototransistor when the C arm is removed, that is, when it is not connected. In FIGS. 21A and 21B, the control signal is in the "Hi" state when the C arm is connected, and in the "Lo" state when the C arm is disconnected. FIG. 21B is referred to as a photointerrupter. The wavelength of the light of the light emission diode 991 can be infrared or visible light as long as the light is shaded from the surrounding light. However, when the surrounding light (fluorescent light) enters, it is desired that an infrared LED is used.

In FIG. 18, the C arm 906 is connected to the flat panel X-ray detector 913 through the extension cable 917. However, if there is a connector having the same function as the connector 911, a connection can be made to the connector.

For example, a connection can be made to the connector of the mobile X-ray generation apparatus 13 provided with wheels as illustrated in FIG. 20.

The mechanical connection between the C arm 906 and the flat panel X-ray detector 913 is made by the fixing hook 912. They are fixed with hook in the groove on the side of the housing of the flat panel X-ray detector 913.

In the non-connecting state radiographing, a cable can interfere with the radiographing and a hand or a foot can touch and destroy the flat panel X-ray detector 913 in the act of radiographing. Therefore, a no-cable system (cable less) is desired. A drive signal input to the flat panel X-ray detector 913 can be externally controlled by wireless communication by providing a wireless interface and an antenna in the flat panel X-ray detector 913. Otherwise, wireless communications can be stopped, and a timing generation unit and a control unit can be provided in the flat panel X-ray detector 913. The digital signal with image information from the flat panel X-ray detector 913 can also be used in the wireless communication, and a storage unit capable of accumulating radiographing data on the flat panel X-ray detector 913 and easily attached and removed such as USB memory, an MO disk, a hard disk, etc. can be provided.

In the non-connecting state radiographing, to attain a cableless system, it is necessary to provide a power supply (battery) for the flat panel X-ray detector 913 at the inside of the flat panel X-ray detector 913. The connecting state radiographing performed when the C arm 906 is connected uses the power supply of the X-ray radiographing apparatus. The non-connecting state radiographing is driven by a battery provided in the flat panel X-ray detector 913. It is desired that the battery has a large capacity and can be charged. However, a larger capacity has the problem of a heavier system. The flat panel X-ray detector 913 requested in the non-connecting state radiographing is a light and easily portable unit. Therefore, a necessary battery has to be smaller in capacity to a certain extent. According to the present mode for embodying the present invention, these conditions can be satisfied. That is, the present mode for embodying the present invention for driving the non-connecting state radiographing with suppressed heat generation improves the battery system required in realizing a cableless system.

The modes for embodying the present invention have been described above, and the terms are defined as follows. The fluoroscopic radiographing is synonymous with moving image radiographing, and an observer can continuously observe X-ray images in real time through a monitor and the like, or the X-ray images can be temporarily stored on a storage medium as digital data, then separately regenerated, and observed by a monitor. All or a part of the fluoroscopic radiograph image data stored on the storage medium can be printed on paper or film, and can be observed as a plurality of still images.

Similarly, the still image radiographing is performed, that is, the images can be observed as is by a monitor, or observed after stored in memory, whichever can be optionally selected.

The flat panel X-ray detector 913 has the structure of the radiation detection substrate 101, the drive circuit unit 103, the read out circuit unit 102, and the AD conversion unit 105 adhered to the support plate 914 or fixed by a screw. The structure is covered with a covering member for covering the entire structure.

The radiation incident plane of the covering member is made from the material mainly composed by carbon, and the portions other than the radiation incident plane are made of any of magnesium, aluminum, stainless steel, and plastic. The support plate is made of any of magnesium, aluminum, stainless steel, and plastic.

The flat panel X-ray detector 913 is provided with at least one handle portion for portability. The flat panel X-ray detector 913 is provided with a battery, and power is supplied from the power supply wiring via the C arm 906 during the connecting state radiographing. In the non-connecting state radiographing, power is supplied from the battery. The battery is designed to be easily removed.

The flat panel X-ray detector 913 is provided with memory, outputs data through electric wiring for data transfer via the C arm 906 in the connecting state radiographing. In the connecting state radiographing, data is accumulated in the memory. The memory can be easily removed. During the connecting state radiographing, the radiographing can be performed with electric wiring connected via the C arm 906. During the non-connecting state radiographing, the radiographing can be performed with the C arm 906 completely disconnected.

The radiation detection element PD includes a wavelength conversion element for converting radiation into visible light, an optoelectronic conversion element for receiving visible light and converting it into an electrical signal. The wavelength conversion element is configured mainly by at least one of $Gd_2O_3$, $Gd_2O_2S$, and CsI. The optoelectronic conversion element is configured mainly by amorphous silicon.

The radiation detection element PD is mainly made of any of selenium (Se), gallium arsenide (GaAs), silver iodide (HgI2), lead iodide (PbI2), zinc sulfide (ZnS), zinc selenium (ZnSe), cadmium tellurium (CdTe), lead tellurium (ZnTe), and combined crystal of tellurium, lead, and cadmium (ZnCdTe), and can be a conversion from radiation directly into electric charge without a phosphor.

In FIGS. 19 and 22, the C arm 16, to which the flat panel X-ray detector 11 and the radiation source 12 are connected, is connected to a wagon provided with wheels 25. The wagon includes the system controllers 20 and 21 for controlling the radiation source 12 and the flat panel X-ray detector 11, an image processing unit, and a data storage unit, and furthermore the power supply of a radiation source, a power supply of a radiation detection circuit unit, and an heat exchanger for dissipating the heat of the radiation detection circuit unit and the radiation source. Provided outside the wagon is at least one monitor 22 capable of observing an image radiographed by the flat panel X-ray detector 11. At the connection point between the wagon and the C arm 16, the C arm 16 has the mechanism of allowing back and forth, right and left, up and down movement and rotation.

A convenient X-ray imaging apparatus can be provided as a device capable of performing not only the fluoroscopic radiographing performed in the state in which the C arm is connected and the radiographing of a still image, but also the radiographing performed in the state in which the C arm is disconnected. If the radiographing can be performed with the X-ray detector removed from the C arm, not only the X-ray source connected to the C arm, but also the X-rays separately provided in the radiographing room can be used. Therefore, not only the convenience, but also the image quality can be improved. During the non-connecting state radiographing, it is advantageous in driving using a battery because the drive is performed with suppressed power consumption. Furthermore, in the non-connecting state radiographing, a cableless cassette as well as a film cassette can be used.

The above-mentioned modes for embodying the present invention indicate practical examples of embodying the present invention, and the technical scope of the present invention is not restricted. That is, the present invention can be embodied in variations within the technical concepts, gist, and characteristics of the present invention.

Furthermore, the present invention includes the embodiment realized by operating various devices according to the program stored in a computer (CPU or MPU) of the system or the device to realize the functions of the above-mentioned modes for embodying the present invention, and operating the computer in a device or a system connected to the various devices to provide a program code of software for realizing the function of the modes for embodying the present invention from the storage medium or through a transmission medium such as the Internet and the like.

In this case, the program code itself of the software realizes the functions of the modes for embodying the present invention, and the program code itself, the unit for supplying the program code to the computer, for example, a storage medium storing the program code configure the present invention. A storage medium storing the program code can be, for example, a flexible disk, a hard disk, an optical disk, an magneto optical disk, CD-ROM, magnetic tape, a non-volatile memory card, ROM, etc.

The modes for embodying the present invention also include not only the case in which the functions described by referring to the above-mentioned modes for embodying the present invention are realized by executing the provided program code by the computer, but also the case in which the functions described by referring to the above-mentioned modes for embodying the present invention with the OS (operating system) or other application software operating in the computer including the program code are realized.

Furthermore, the present invention also includes the case in which the functions of the modes for embodying the present invention are realized by the process of storing a supplied program code in memory in a feature expansion board of a computer and a feature expansion unit connected to the computer, and performing all or a part of the actual process by the CPU and the like provided in the feature expansion board and the feature expansion unit according to the instruction of the program code.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-118324, filed on Apr. 21, 2006, which is hereby incorporated by reference herein in its entirety.

What is claimed is:

1. A radiation imaging apparatus, comprising:
a flat panel detector;
a holding unit for holding at least the flat panel detector; and
a control unit for controlling the flat panel detector, wherein
the flat panel detector can be connected to and disconnected from the holding unit,
connecting state radiographing can be performed with the flat panel detector connected to the holding unit, and non-connecting state radiographing can be performed with the flat panel detector disconnected from the holding unit, and
the control unit controls the flat panel detector such that a heat generation quantity of the flat panel detector during the non-connecting state radiographing can be lower than a heat generation quantity of the flat panel detector during the connecting state radiographing.

2. The radiation imaging apparatus according to claim 1, wherein
the control unit controls the flat panel detector such that power consumption of the flat panel detector during the non-connecting state radiographing can be lower than power consumption of the flat panel detector during the connecting state radiographing.

3. The radiation imaging apparatus according to claim 2, wherein
the flat panel detector comprises: picture elements, arranged in a matrix of rows and columns on a substrate, including conversion elements for converting radiation into an electrical signal and switch elements; drive wiring connected to the switch elements in a row direction; signal wiring, connected to the plurality of switch elements in a column direction, for transmitting the electrical signal; driving circuit unit connected to the drive wiring; and a read out circuit unit connected to the signal wiring, wherein
the control unit controls the flat panel detector such that power consumption of the read out circuit unit in the non-connecting state radiographing can be lower than power consumption of the read out circuit unit in the connecting state radiographing.

4. The radiation imaging apparatus according to claim 3, wherein
the control unit controls the flat panel detector such that power supply voltage of the read out circuit unit in the non-connecting state radiographing can be lower than power supply voltage of the read out circuit unit in the connecting state radiographing.

5. The radiation imaging apparatus according to claim 3, wherein the read out circuit unit comprises an amplifier, and
the control unit controls the flat panel detector such that an amount of current of a constant current source of the amplifier in the non-connecting state radiographing can be lower than an amount of current of a constant current source of the amplifier in the connecting state radiographing.

6. The radiation imaging apparatus according to claim 2, wherein the flat panel detector comprises:
picture elements, arranged in a matrix of rows and columns on a substrate, including conversion elements for converting radiation into an electrical signal and switch elements;
drive wiring connected to the switch elements in a row direction;
signal wiring, connected to the plurality of switch elements in a column direction, for transmitting the electrical signal;
a driving circuit unit connected to the drive wiring; and
a read out circuit unit connected to the signal wiring,
wherein the control unit controls the flat panel detector such that a bias of the conversion element or a drive voltage of the switch element in the non-connecting state radiographing can be lower than a bias of the conversion element or a drive voltage of the switch element in the connecting state radiographing.

7. The radiation imaging apparatus according to claim 2, wherein the flat panel detector comprises:
picture elements, arranged in a matrix of rows and columns on a substrate, including conversion elements for converting radiation into an electrical signal and switch elements;
drive wiring connected to the switch elements in a row direction;
signal wiring, connected to the plurality of switch elements in a column direction, for transmitting the electrical signal;
a driving circuit unit connected to the drive wiring; and
a read out circuit unit connected to the signal wiring,
wherein the control unit controls the flat panel detector such that the read out circuit unit corresponding to picture elements included in a radiation irradiation area and the driving circuit unit are operated, and the read out circuit unit corresponding to picture elements in an area other than the radiation irradiation area and the driving circuit unit are not operated or current consumption is reduced.

8. The radiation imaging apparatus according to claim 1, wherein
the flat panel detector comprises a heat dissipation transmission unit for transmitting generated heat to the holding unit and dissipating heat in a state in which the detector is connected to the holding unit.

9. The radiation imaging apparatus according to claim 1, wherein
the flat panel detector can perform moving image radiographing and still image radiographing in the connecting state radiographing, and can perform idling drive and still image radiographing in the non-connecting state radiographing.

10. The radiation imaging apparatus according to claim 1, further comprising:

a connection detection unit for detecting whether or not the flat panel detector is connected to the holding unit, wherein the control unit controls the flat panel detector on a basis of a result of detection by the connection detection unit.

11. A method of controlling a radiation imaging apparatus having a flat panel detector, a holding unit for holding at least the flat panel detector, the flat panel detector being connectable to and disconnectable from the holding unit, the apparatus performing connecting state radiographing with the flat panel detector connected to the holding unit, and performing non-connecting state radiographing with the flat panel detector disconnected from the holding unit, wherein the flat panel detector is controlled such that a heat generation quantity of the flat panel detector during the non-connecting state radiographing can be lower than a heat generation quantity of the flat panel detector during the connecting state radiographing.

12. The method according to claim 11, wherein the control unit controls the flat panel detector such that power consumption of the flat panel detector during the non-connecting state radiographing can be lower than power consumption of the flat panel detector during the connecting state radiographing.

13. A computer-readable storage medium storing a program, used to direct a computer to control a radiation imaging apparatus, allowing the computer to control the radiation imaging apparatus having a flat panel detector, a holding unit for holding at least the flat panel detector, the flat panel detector being connectable to and disconnectable from the holding unit, the apparatus performing connecting state radiographing with the flat panel detector connected to the holding unit, and performing non-connecting state radiographing with the flat panel detector disconnected from the holding unit, wherein the program allows the computer to control the flat panel detector such that a heat generation quantity of the flat panel detector during the non-connecting state radiographing can be lower than a heat generation quantity of the flat panel detector during the connecting state radiographing.

14. The computer-readable storage medium according to claim 13, wherein the program allows the computer to control the flat panel detector such that power consumption of the flat panel detector during the non-connecting state radiographing can be lower than power consumption of the flat panel detector during the connecting state radiographing.

* * * * *